United States Patent [19]

Yamanishi et al.

[11] Patent Number: 4,986,665
[45] Date of Patent: Jan. 22, 1991

[54] OPTICAL DENSITY DETECTOR

[75] Inventors: Akio Yamanishi; Hitoshi Kamezawa; Takao Sakai; Sadafusa Tsuji; Mitsunobu Ota, all of Osaka, Japan

[73] Assignee: Minolta Camera Kabushiki Kaisha, Osaka, Japan

[21] Appl. No.: 227,999

[22] Filed: Aug. 3, 1988

[30] Foreign Application Priority Data

| Aug. 6, 1987 | [JP] | Japan | 62-197397 |
| Aug. 19, 1987 | [JP] | Japan | 62-206688 |
| Aug. 20, 1987 | [JP] | Japan | 62-206791 |
| Aug. 20, 1987 | [JP] | Japan | 62-206792 |
| Aug. 20, 1987 | [JP] | Japan | 62-206793 |
| Aug. 20, 1987 | [JP] | Japan | 62-206795 |
| Aug. 20, 1987 | [JP] | Japan | 62-206797 |
| Aug. 20, 1987 | [JP] | Japan | 62-206798 |
| May 13, 1988 | [JP] | Japan | 63-117197 |
| May 13, 1988 | [JP] | Japan | 63-117198 |

[51] Int. Cl.$^5$ .......................................... G01N 21/27
[52] U.S. Cl. ...................... 356/402; 356/407; 356/420; 356/425; 250/226
[58] Field of Search .................. 356/40, 41, 51, 402, 356/406, 407, 409, 420, 425; 250/214 C, 226

[56] References Cited

U.S. PATENT DOCUMENTS

| 3,910,701 | 10/1975 | Henderson et al. | 356/73 |
| 4,167,331 | 9/1979 | Nielsen | 356/41 |
| 4,295,042 | 10/1981 | Watanabe et al. | 250/226 |
| 4,312,593 | 1/1982 | Baker et al. | 356/418 |
| 4,684,245 | 8/1987 | Goldring | 356/41 |
| 4,832,491 | 5/1989 | Sharpe et al. | 250/214 C |

FOREIGN PATENT DOCUMENTS 282245 12/1987 Japan .................................. 356/402
WO88/01150 2/1988 PCT Int'l Appl. .

Primary Examiner—F. L. Evans
Attorney, Agent, or Firm—Price, Gess & Ubell

[57] ABSTRACT

An optical density detector which comprises a first light source for emitting a first light which belongs to a wavelength region in which the first light is hardly absorbed by a specific material contained in a sample, a second light source for emitting a second light which belongs to a wavelength region in which the second light is absorbed, substantially as compared with the first light, by the specific material, wherein a peak-wavelength of the second light is shifted by change of a temperature and change of an absorption of the specific material caused by the peak-wavelength shift is characteristic of a linear equation with a gentle grade, light receiving device for measuring a quantity of the first and the second lights which are transmitted through the sample, an arithmetic unit for calculating difference of absorbance between the first light and the second light of which both change depending on the density of the specific material, a temperature measuring device for measuring the temperature of the first and the second light sources and the light receiving device, or measuring the ambient temperature around the first and the second light sources and the light receiving device and compensation unit for compensating the difference of absorbance which is calculated by the arithmetic unit, with the absorption coefficient of the specific material at a shifted peak-wavelength of the second light, wherein the shifted peak-wavelength is calculated on the basis of a measured value measured by said temperature measuring device.

26 Claims, 22 Drawing Sheets

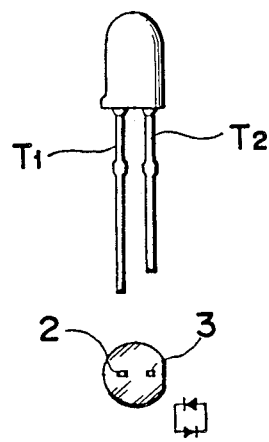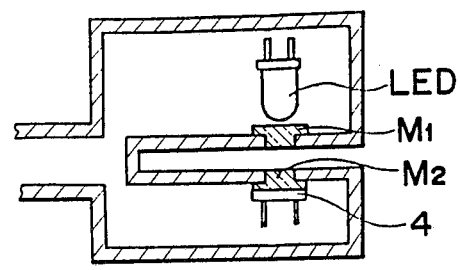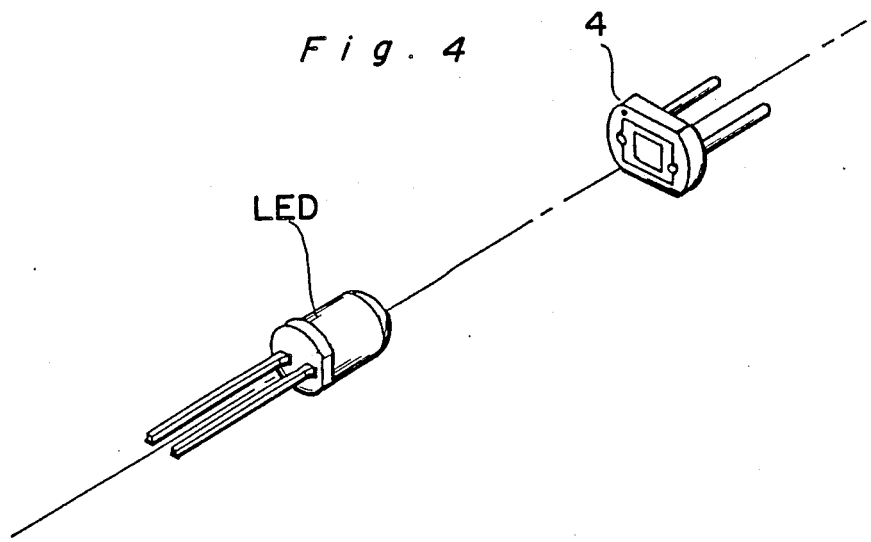

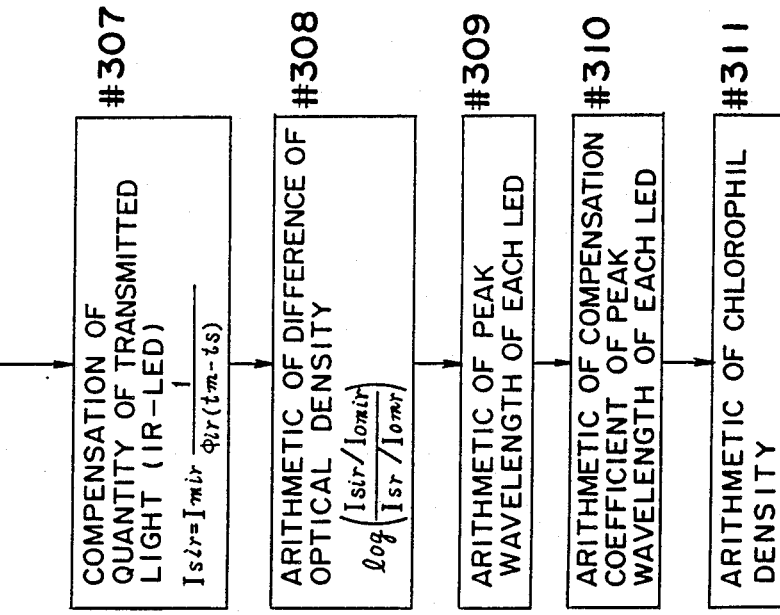
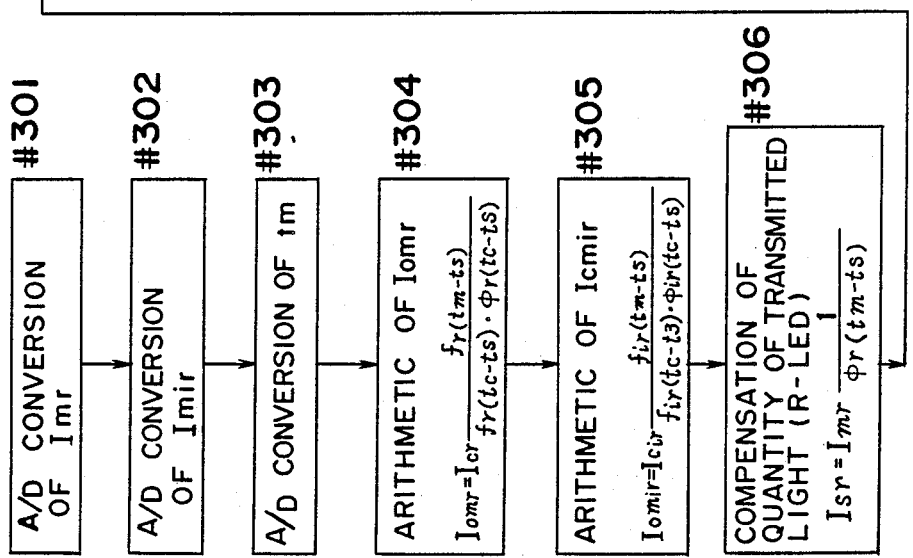
Fig. 21

OPTICAL DENSITY DETECTOR

BACKGROUND OF THE INVENTION

1. Field of the invention

The present invention generally relates to an optical type density detector for measuring the density of a specific material contained in a material object by utilizing a difference of light absorption degree on each wavelength, which respective materials have, and more particularly relates to a portable detector for measuring a chlorophyl density contained in green leaves.

2. Description of the related art

A chlorophyl quantity contained in green leaves of a plant relates closely to do with its plant breeding and soil as well as a manuring method and a quantity of manure. Therefore, it is possible to diagnose whether or not the degree of growth of the plant is sufficient by measuring of the contained chlorophyl quantity. Thereupon, measurement of the quantity of the contained chlorophyl in the leaves is usually made to effectively provide manure, in order to promote the growth of the plant and increase a yield of the crops. A measuring method of the prior art involves, cutting a certain area in the green leaf away, and steeping it in a solvent (Acetone) for about forty-eight hours, and extracting the chlorophyl after separating it from the green leaf, and then obtaining data of the quantity of the contained chlorophyl resulting from spectrometry. There is a disadvantage that measurement by this method causes a green leaf to be hurt as well as requires spending a lot of time.

Accordingly, a device which enables the farmer to obtain data of the contained chlorophyl in a few seconds without hurting the green leaf has been put into practical use. The above-mentioned device enables the farmer to measure optically the quantity of the contained chlorophyl in the leaves with the transmitted light which comes through the green leaf at the time when an artificial light irradiates the leaf. FIG. 33 shows a basic system of chlorophyl measuring. In FIG. 33, a reference numeral 200 designates a light source such as a xenon tubing and/or a tungsten lamp. The light emitted from the xenon tubing 200 is illuminated to a sample of a leaf L through a fiber tube 201. The emitted light is transmitted through the leaf L, and the transmitted light is led to a dichroic mirror 203 through a fiber tube 202. By the dichroic mirror 203, a light belonging to the infrared region and a light belonging to the red color region are, respectively, separated from the transmitted light. The respective lights are led to the respective light receiving elements 205, 204. The respective light receiving elements measure each quantity of the respective lights. A theory of measuring a chlorophyl density is well-known and described later on. The chlorophyl density is calculated on the basis of the abovementioned respective transmitted light quantities and light quantities received at each light receiving element 204, 205 at the time when measuring without the sample.

One of the devices as described above is provided with a measuring head having a slit in which the green leaf as the sample to be measured is inserted, and a body of the device, in which both a unit for doing a computing processing for obtaining the quantity of the contained chlorophyl resulting from measuring the transmitted light which comes through the green leaf and a circuit for indicating output data from the unit are accommodated. In this device, a tungsten lamp is provided as an artificial light source. Due to utilizing the tungsten lamp, luminous intensity of the light emitted from the light source is not sufficient, so that it is necessary to provide a member isolated from a light coming from outside because the light emitted from the tungsten lamp is easily influenced by the light coming from outside. Therefore, handling of the device is troublesome.

On the other hand, another type of the device has been already disclosed. That is, the device is provided with a lamp generating a large amount of the light quantity, and a computing unit. The above-mentioned lamp as the light source is a flash tube for emitting a flashing light in order to obtain a large amount of the stabilized light, and the computing unit is so designed that a logarithmic arithmetic necessary for obtaining the quantity of the contained chlorophyl is easily carried out by inserting a damping period of the light quantity into an exponential function. Whereby, stability on an electrical circuit is improved as well as no adjustment for measurement is requested each time the device is used for measurement. However, this device has a disadvantage in that an electrical power circuit for the light source is complicated and a production cost of the device arises, as well.

Furthermore, if the lamp to be utilized in the device as the light source has a character that the quantity of the light emitted from the lamp is changing in response to an ambient temperature, the measured results do not become accurate, owing mainly to dispersion of the light quantity due to the temperature. So one point of importance for the measuring device is that the device has high reliability so that all the measured results measured by the device under any circumstances are always accurate. Another point of importance for the device is that the device can be easily utilized to make measurements. That is why something must be done not only to maintain high reliability and good operability of the device, but also to ensure simplification for the device as well as the improvement of the cost-performance for the device.

SUMMARY OF THE INVENTION

The invention has been made in view of the above described problems. It is a first object of the present invention to measure the density of a specific material contained in a sample with high accuracy even if a quantity of light from a light source changes under the influence of a temperature change. It is a second object of the present invention to improve an operability of a device as well as to make the device smaller.

In accomplishing these and other objects, there is provided an optical density detector comprising a first light source for emitting a first light which belongs to a wavelength region in which said first light is hardly absorbed by a specific material contained in a sample, and a second light source for emitting a second light which belongs to a wavelength region in which the second light is absorbed, relatively much as compared with the first light, by the specific material. The peak-wavelength of the light is shifted by a change of temperature and the change of an absorption coefficient of the specific material, caused by said peak-wavelength shift is characteristic of a linear equation with a gentle grade. A light receiving means for measuring a quantity of the first and said second lights which are, respectively, transmitted through the sample is provided. Arithmetic means for calculating a difference of absorbence between the first light and the second light of which both change depending on the density of the specific material, is used on the measured values measured by the light receiving means. A temperature measuring means for measuring a temperature of the first and the second light sources and the light receiving means, or measuring an ambient temperature around the first and the second light sources and the light receiving means is operatively connected with compensation means for compensating the difference of absorbence which is calculated by the arithmetic means, with an absorption coefficient of the specific material at a shifted peak-wavelength of the second light, wherein the shifted peak-wavelength is calculated on the basis of a measured value measured by the temperature measuring means.

Accordingly, before measuring the density of the specific material, an initial calibration is made without the sample for the first and the second light sources. After that, the first and the second lights are emitted, and each quantity of the first and the second lights transmitted through the sample is measured by the light receiving means. The arithmetic means computes the difference of the absorbence on each light, being proportional to the density of the specific material, on the basis of the measured value measured by the light receiving means because the absorption of the light by the specific material is different, i.e., the first light is absorbed by the specific material much less that the second light is absorbed. On one hand, the temperature measuring means measures the temperature change of the first and the second light sources and the light receiving means between the calibration stage and the measuring stage. The compensation means compensates the difference of the absorbence which is calculated by the arithmetic means with the absorption coefficient of the specific material on the peak-wavelength which has been shifted. The absorption coefficient is characteristic of the linear equation, so that the absorption coefficient can be easily calculated since the equation is memorized.

If each quantity of the light emitted from the first and the second light sources, especially the quantity of the light from the second light source, changes under the influence of the temperature change, a measured value with high accuracy can be obtained after compensation for the temperature change. The above-mentioned compensation can be carried out without a data table for the compensation, which is stored in a memory device. As a matter of course, the compensation with the data table can be effective if the detector has a big capacity of a memory device.

BRIEF DESCRIPTION OF THE DRAWINGS

These and other objects and features of the present invention will become apparent from the following description taken in conjunction with the preferred embodiment thereof with reference to the accompanying drawings, in which:

FIG. 2 is a side elevation view and a front elevation view, respectively showing an LED as a light source utilized in the detector;

FIG. 4 is a perspective illustration showing a construction of an optical system of the detector;

FIG. 5 is a partially expanded sectional view showing a part around a measuring head section of the detector;

FIG. 21 is a flow chart of a subroutine which is carried out at step #109 in FIG. 19;

DETAILED DESCRIPTION OF THE INVENTION

Figure 1:
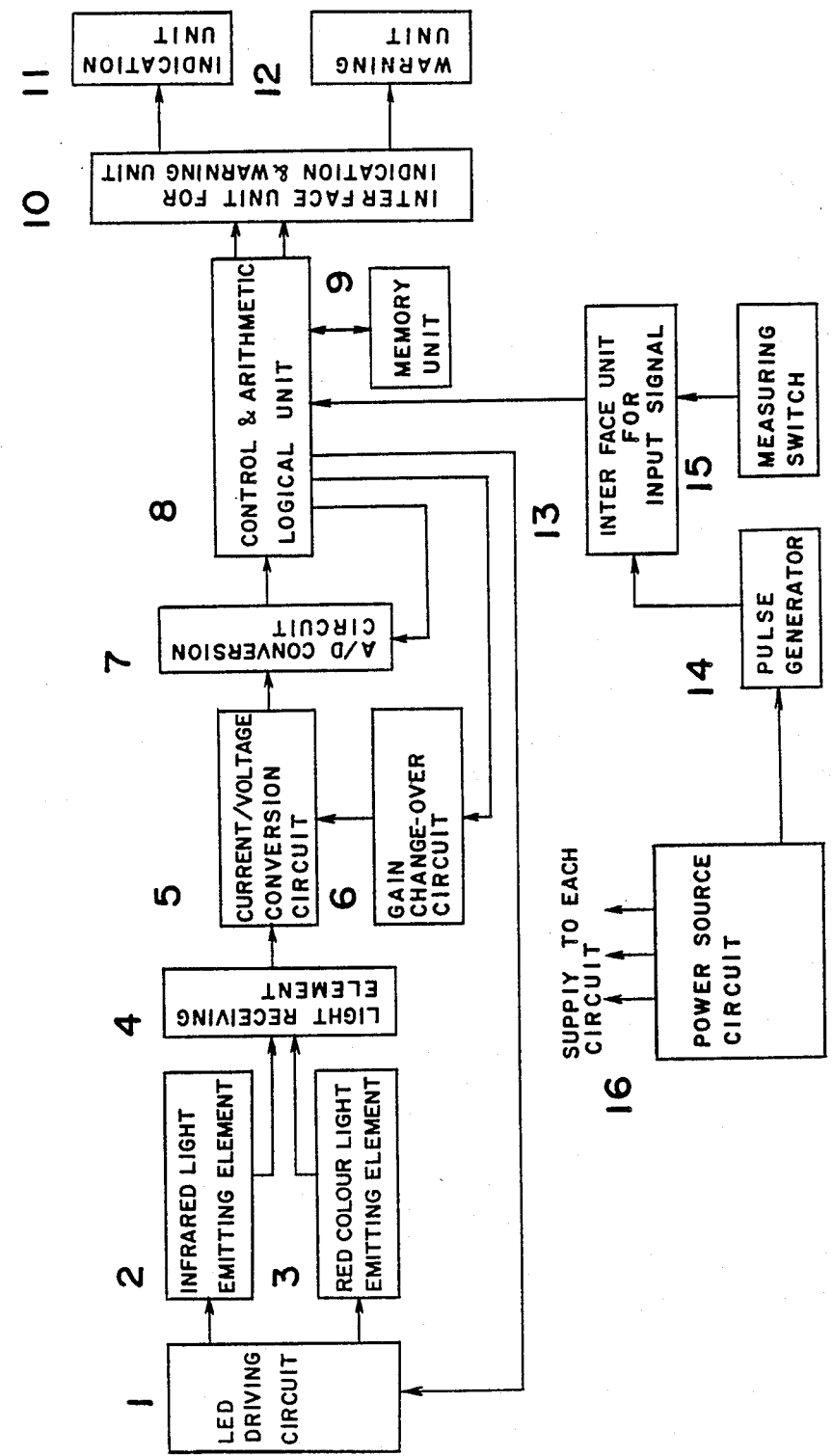
FIG. 1 is a block diagram showing components of a chlorophyl detector according to one preferred embodiment of the present invention.

Before the description of the present invention proceeds, it is to be noted that like parts are designated by like reference numerals and symbols throughout the several views of the accompanying drawings.

Figure 10:
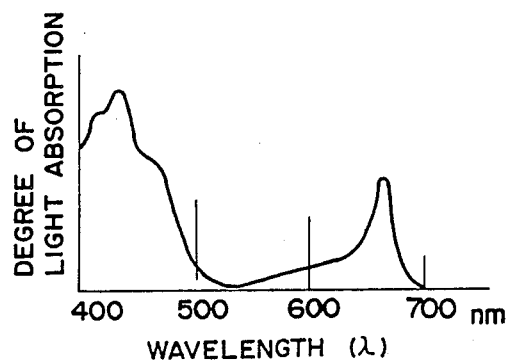
FIG. 10 is a graph showing absorbence characteristic on a chlorophyl.

Referring now to FIG. 10, there is shown an absorbence characteristic on a chlorophyl. As it becomes apparent from the drawing, the chlorophyl extremely absorbs light belonging to a blue color region as well as light belonging to a red color region, while a light belonging to a green color region is slightly absorbed by the chlorophyl. Especially, the chlorophyl can scarcely absorb light belonging to an infrared region. Thus, the chlorophyl has a characteristic, that is described above, on absorption of light. Measurement of the contained chlorophyl in green leaves on the difference between the respective absorbence of two lights which, respectively, belong to wavelength regions where the light is extremely absorbed by the chlorophyl and where the light can be hardly absorbed by the chlorophyl. Generally, as the wavelength regions to be used for measuring in practice, the red color region to which the light which is scarcely influenced by a carotene (a yellow pigment) belongs and the infrared region are most suitable for the regions to be used. Therefore, lights which belong to the abovementioned regions are used in this embodiment. That is, a chlorophyl detector which is one of optical type density detectors as one preferred embodiment to which the present invention are applicable is so designed that the contained chlorophyl in a green leaf is detected by measuring a degree of absorption of the light belonging to the red color region, compared with a light as a reference light which is scarcely influenced by the chlorophyl, i.e., a light belonging to the infrared region.

Referring now to FIG. 2, there is shown light emitting elements such as a LED 2,3 or the like which are packaged into one unit. One of them 2, is a light emitting diode for emitting the infrared light, and the other, 3, is a light emitting diode for emitting the red color light. In this embodiment, two light emitting diodes 2,3 are connected to each other, so as to have an opposite polarity. Whereby, it is possible to control whether the light emitting diode 2 for emitting the infrared light is actuated or the light emitting diode 3 for emitting the red color light is actuated, depending on the direction of a current to be applied to respective terminal $T_1$, $T_2$. On one hand, a light emitting element comprising a type of three terminals, of which either a cathode or an anode is in common can be applicable to the present invention for proper execution. Besides, proper execution of the present invention is made even though the packaged element described above comprises a pair of elements which comprises a light emitting diode for emitting the red color light and a light emitting diode for emitting the infrared light of which both are, respectively, enclosed in a smaller package.

Figure 3:
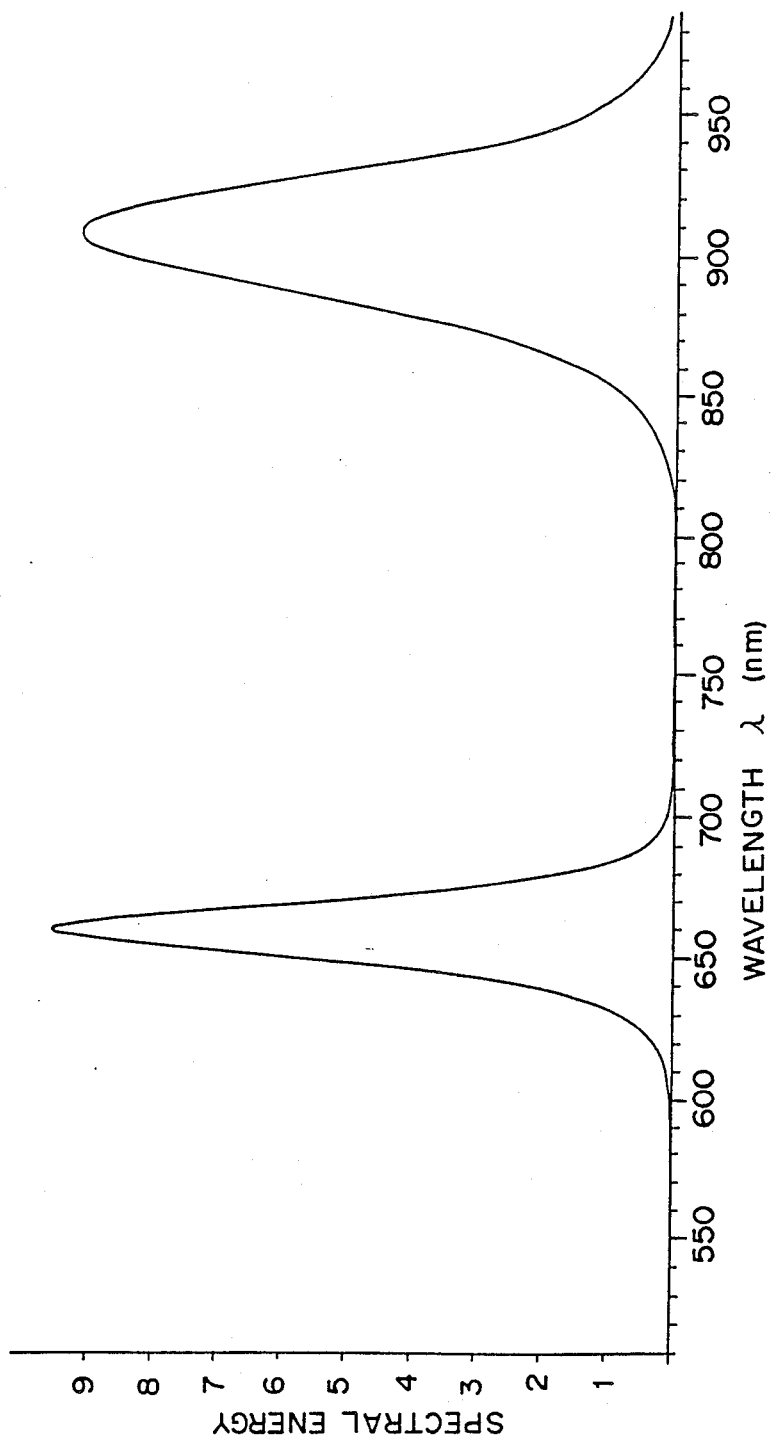
FIG. 3 is a diagram showing a spectral energy characteristic of the LED.

Referring now to FIG. 3, there is shown a spectral characteristic of the emitted light energy of both light emitting diodes 2,3. As seen clearly from the drawing of FIG. 3, the light emitting diode 3 for emitting a red color light has a spectral energy of which a peak is distributed around 650 nm to 670 nm in wavelength. And if comparing with an absorbence of the chlorophyl shown in FIG. 10, the peak of the wavelength accords with the other peak of the wavelength on absorbence. In addition, the light emitting diode 2 for emitting the infrared light has a spectral energy of which a peak is distributed around 880 nm to 940 nm in wavelength, so that the infrared light is suitable for taking charge of measurement at a spectra band where a light is scarcely absorbed by the chlorophyl.

Referring to FIG. 4, there is shown an optical system according to this embodiment of the present invention. In FIG. 4, a reference character LED designates a pair of the light emitting elements which is shown in FIG. 2, i.e. One is the light emitting diode of emitting the red color light and the other is the light emitting diode for emitting the infrared light. And also, a single light receiving element 4 is arranged to face the abovementioned LED, so it is so designed that between the LED and the light receiving element 4 a green leaf as a sample is inserted. That is, it is designed to make a measuring system of a so-called transmission type.

Referring now to FIG. 5, there is shown an arrangement of the optical system according to this embodiment as drawn by a cross sectional view. In FIG. 5, members $M_1$, $M_2$ having a T-shaped cross section, which is, respectively, located in front of the light emitting diode LED and the light receiving element 4 correspondingly, are protectors for preventing drop of water and/or dust from coming into a measuring path. In addition to the above, it is possible to make the members $M_1$, $M_2$ have a diffusivity characteristic, if necessary, so as to mix up the infrared light with the red color light. Instead of the above-mentioned arrangement, it is preferable that it is so designed to permit the light emitting diode LED and the light receiving elements 4 to be located closer to each other at a common wall and the element 4 can receive a light, i.e., the reflected light, which is emitted by the light emitting diode LED and is reflected on the green leaf.

Referring now to FIG. 1, the main components, as drawn by a block diagram, are In this embodiment, each light emitting diode 2,3 is actuated with time division so that a single light receiving element 4 outputs two signals with a different frequency. Another method for generating two signals with a different frequency is available. For example, two kinds of light emitting diodes having a different wavelength of the emitting light from each other are activated at the same time with a different frequency, then an output signal of a single light receiving element is filtered through a certain processing of frequency separation, and two signals with a different frequency are reproduced. However, in this embodiment, it is limited to an explanation as to the time division method. First, a reference numeral 1 designates a LED driving circuit for controlling emission of both light emitting diodes 2,3. This LED driving circuit 1 controls the supply of an electrical current to both the light emitting diode 2 for emitting the infrared light and the light emitting diode 3 for emitting the red color light. The light emitted by each diode 2,3 is transmitted through the green leaf of a measured object. After that, the light receiving element 4 receives the transmitted light. The light receiving element 4 generates photo-electric current corresponding to the quantity of the received light, then the photo-electric current is converted into a corresponding voltage by a current-voltage conversion circuit 5. A gain change-over circuit 6 controls gain of the current-voltage conversion circuit 5 by an order from a control and arithmetic logical unit 8 in accordance with transmittance of the green leaf of the measured object or zero-point adjustment at a power on. An output of the current-voltage conversion circuit 5, which is converted from the respective photo-electric currents corresponding to the infrared light and the red color light, is converted into a digital signal through an A/D conversion circuit 7. A memory unit 9 comprises a RAM backed up or a non-volatile RAM. The memory unit 9 automatically memorizes a value which is measured by each emission of the respective light emitting diodes 2,3 for emitting the infrared light and for emitting the red color light, when the power is on, a zero-point state means that the measured object is not inserted yet, and the memorized value in the memory unit 9 is used as a reference value for detecting whether or not an initial error exists the next time the power is on. An interface unit 10 has a function for making a value corresponding to the chlorophyl density as well as indications for warning troubles of measuring indicated in a indication unit 11 and warning unit 12, respectively. The above-mentioned value corresponding to the chlorophyl density is calculated by arithmetic of a logarithm of a ratio between the receiving light quantity of the infrared light and the receiving light quantity of the red color light, of which both are computed by the control and arithmetic logical unit 8. An interface unit 13 for an input signal is an interface for inputting a signal which is generated pulsewise at power-on and a signal which is generated by a measuring switch 15 at switch-on to the control and arithmetic logical unit 8. A power source circuit 16 is a circuit for supplying power to the respective circuits described above.

Figure 6:
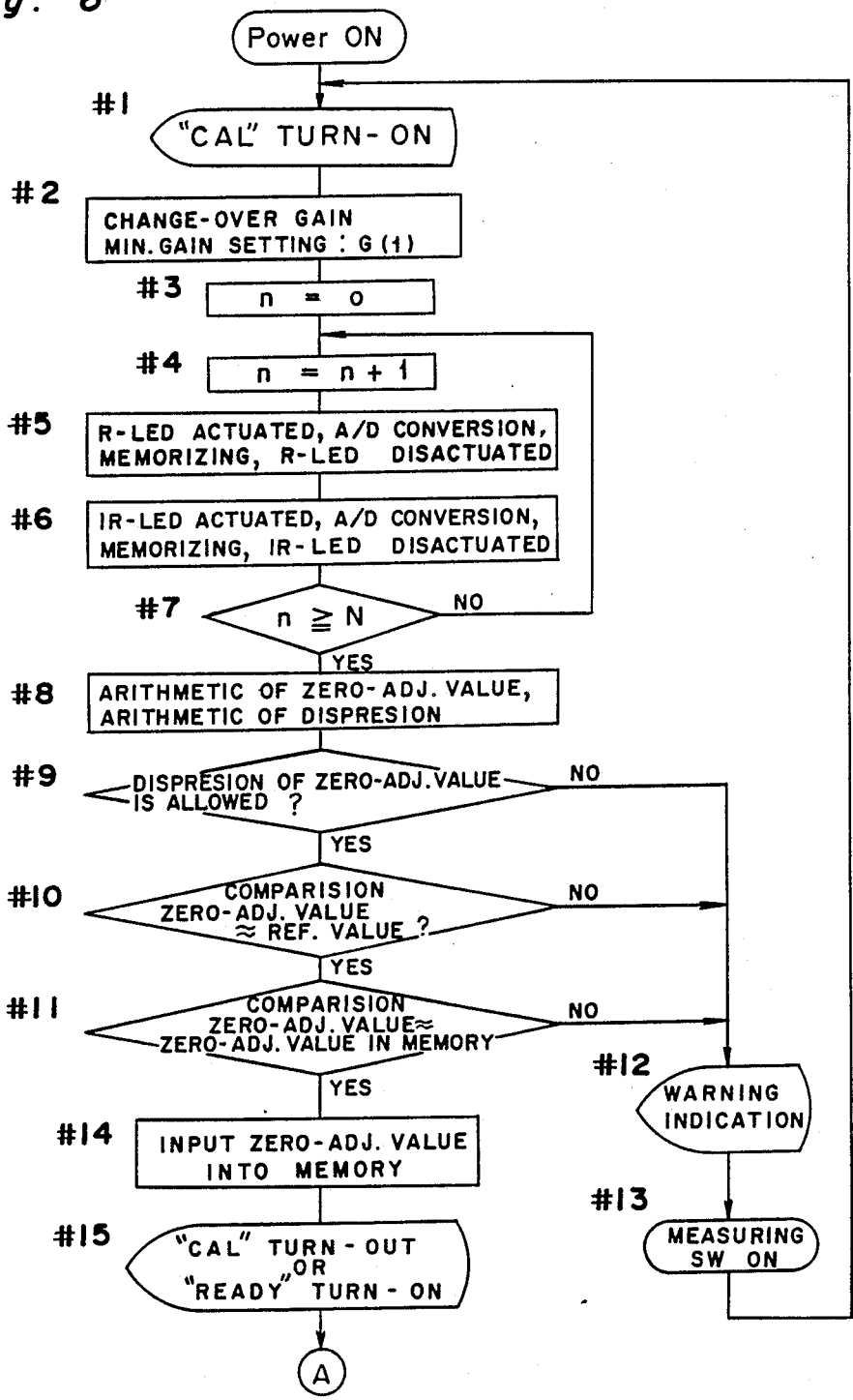
FIG. 6 is a flow chart showing an operation of the detector at the time when an electrical power source of the detector is on, i.e., during a calibrating operation mode.

Next, the detailed explanation of the chlorophyl detector according to an embodiment is described with the drawing of FIG. 6, below. FIG. 6 is a flow chart for showing a procedure during the zero-point adjustment at power-on. In FIG. 6, when the power is on at first, at step #1, it is indicated that it is now executing the zero-point adjustment. After setting gain of the current-voltage conversion circuit 5 to a minimum at step #2, the LED driving circuit 1 is driven so as to turn the light emitting diode 3 for emitting the red color light on at step #5. Furthermore, at the same time, the receiving light quantity received by the light receiving element 4 is converted through the A/D conversion circuit 7, and the conversion value is memorized. After that, the light emitted diode 3 is turned off, i.e., the LED driving circuit 1 is deactivated. Next, the program advances to step #6, and then at step #6, the light emitting diode 2 for emitting the infrared light is turned on by actuating the LED drive circuit 1. At the same time, the light receiving quantity received by the light receiving element 4 is converted through the A/D conversion circuit 7, and the conversion value is memorized. After that, the light emitting diode 2 is turned off, i.e., the LED driving circuit 1 is deactivated. A series of processings regarding turning-on and -off of the respective light emitting diode 2,3 is repeatedly carried out for "N" times (normally it is three to ten times) at steps during step #4 through step #7. After execution of the above, at step #8, the following arithmetic is carried out:

$$\frac{1}{N} \sum_{i=1}^{N} \log \frac{I_{OIRi}}{I_{ORi}} \qquad (1)$$

wherein, $I_{OIRi}$: measured value of the infrared light at the time when the measured object is not yet set (at measurement of No. i);

$I_{ORi}$: measured value of the red color light at the time when the measured object is not yet set (at measurement of No. i).

After execution of the above-mentioned arithmetic, the program advances to step #9. At step #9, arithmetic of a value showing dispersion of the measured value, which is like a standard deviation or difference between a maximum value and a minimum value, is carried out. A purpose of arithmetic of the above-mentioned value showing dispersion is to order a re-measuring once again depending on detecting whether that the measured value is badly influenced by outside factors, if an outside light, for example, a light from a fluorescent lamp or other lights generated by A.C., comes into the measuring path and influences the measured value. Furthermore, in order to detect an influence of the measured value by the outside light in the case that a stationary light as the outside light comes into the measuring path from outside, or in order to detect that unexpected articles come into the measuring path, at step #10, the calculated value according to the equation (1) at the present time is compared with a predetermined reference value memorized in the memory of the control and arithmetic logical unit 8. Besides, at step #11, the calculated value according to the equation (1) at the present time is compared with a reference value which is converted from a value which was calculated at the preceding time. When it is decided at either step #10 or step #11 that the difference between two values is in excess of an allowable range which is predetermined, the program goes to step #1, and it is ordered to re-measure once more, and as the warning indication is made at step #12.

Two types of the comparison at step #10 and step #11 are to be done for the following purposes. The former comparison with the predetermined reference value is concerned with a reliability of the detector. That is, by providing an ensured range for measurement, it is represented that the detector is already beyond its reliability in case the detector requests an operator to remeasure once more under measurement in the circumstance without the outside light. The above-mentioned allowable range is a range to be determined in consideration that the measured value at the zero-point adjustment is changing with a timed deterioration, depending on difference of degradation of luminous intensity for emission with timed deterioration between the light emitting diode 2 for emitting the infrared light and the light emitting diode 3 for emitting the red color light. Therefore, sensitivity for detecting that the outside light of the stationary light influences the measured value during measurement, is not provided. On the other hand, the latter is a range to be determined from the reference value which is a converted value from the preceding measured value so as to eliminate change of the measured value at the zero-point adjustment, on degradation of the light emitting diode with timed deterioration. Therefore, its aim is to detect when the outside light of the stationary light influences the measured value during measurement.

Thus, it is decided whether or not the influence of the outside light such as the stationary light or the A.C. light exists and the reliability of the detector is still maintained as well, and if any one of the results of the above decision is negative, a warning indication is made as well as an indication for ordering re-measurement is made at step #12, and then the program advances to step #13. At step #13, the program is held until the measuring switch 15 is activated by an operator. When it is decided that the measuring switch 15 is ON at step #13, the program goes to step #1, and the zero-point adjustment is executed repeatedly.

In the process from step #9 through step #11, if the end result is positive, then the value which is calculated at this time according to the equation (1) is memorized, and the indication for the zero-point adjustment is turned off or the indication for being ready for measurement is created at step #15.

Figure 7:
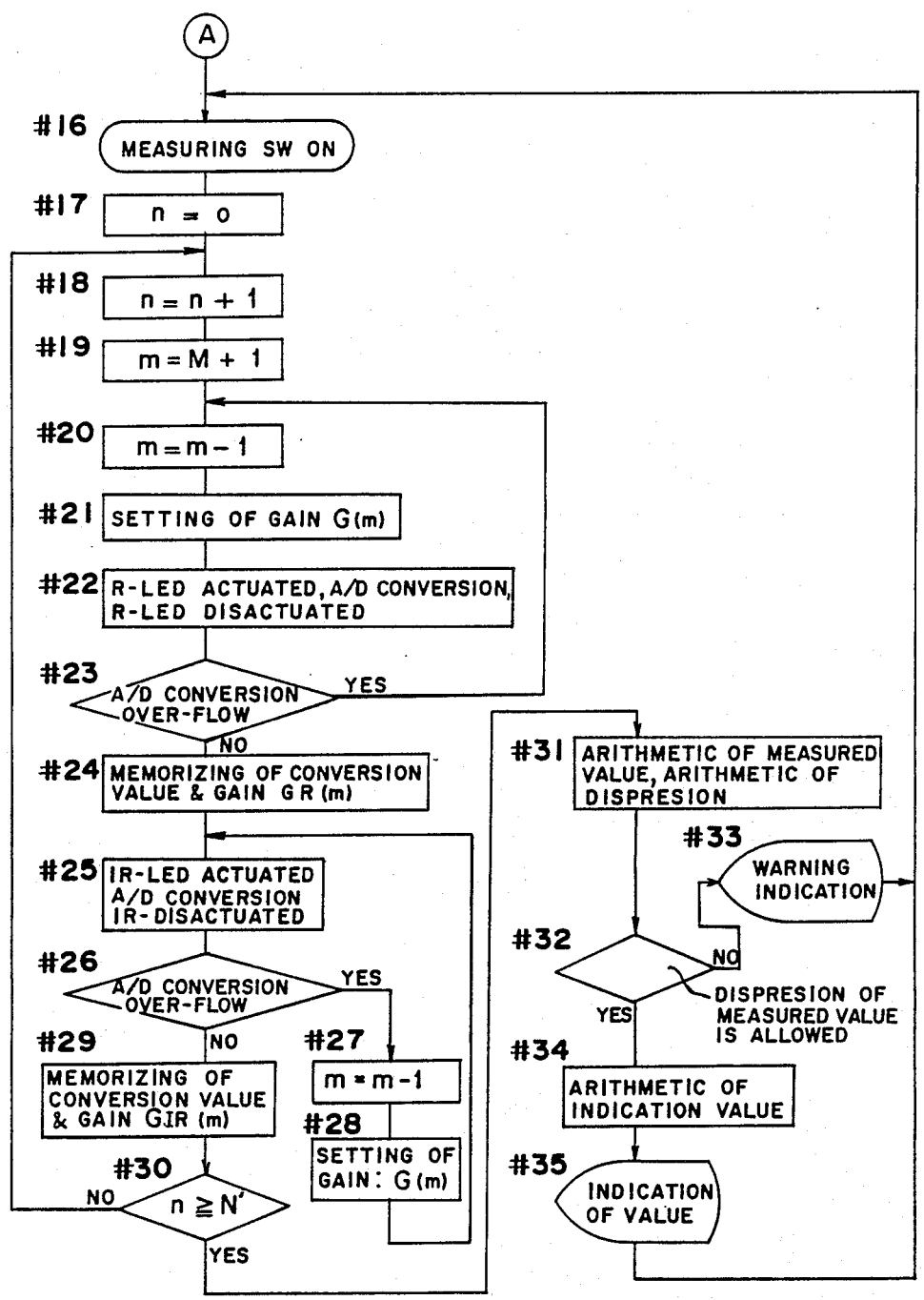
FIG. 7 is a flow chart showing an operation of the detector during a measuring operation mode.

Next, the measuring procedure is explained while referring to FIG. 7. In this embodiment, it is so designed that the measured object of the green leaf is inserted into the optical path for measurement. In FIG. 7, if the measuring switch 15 is made at step #16, the preparation for measurement is made at steps from step #17 through step #20, i.e., counting of a number of measuring. And at step #21, first, gain of the current-voltage conversion circuit 5 is set to the maximum value G(m). Then, at step #22, measurement is made by emission of the light emitting diode 3 for emitting the red color light, i.e., the LED driving circuit 1 is actuated. Next, it is decided at step #23 whether or not the A/D conversion circuit 7 through which the output of the light receiving elements 4 is converted is overflowed against the above gain which is set at step #21. When decided at step #23 that it is overflowed, then, the program goes to step #20. At step #20, gain of the current-voltage conversion circuit 5 is reduced stepwise, and measurement is continued with each gain which is newly set at step #20. When decided at step #23 that it is not overflowed, the A/D conversion circuit 7 outputs the A/D conversion value at step #23, and at step #24, this A/D conversion value and gain G(m) are memorized. Next, at step #25, emission of the light emitting diode 2 for emitting the infrared light is made. At step #26 and step #29, a decision whether or not to overflow, and memorizing of both A/D conversion value and gain are, respectively, made with a similar procedure taken for emission of the red color light as described preciously. Hereupon, gain G(m) to be set for the current-voltage conversion circuit 5 at the time when the light emitting diode 2 for emitting the infrared light is actuated, does not start from gain $G_{(m=M+1)}$ but starts from gain G(m) which has been determined at the time when the light emitting diode 3 for emitting the red color light has been actuated. This is subject to the following reason. Namely, if intensity of emission from both light emitting diodes 2,3 are kept equivalent, the light receiving quantity of the infrared light becomes usually more than the others, as taking absorbence of the chlorophyl into consideration. That is why the above-mentioned manner is taken. However, in case the light emitting quantities of both the light emitting diodes are different, gain G(m) to be set for the current-voltage conversion circuit 5 may be set to gain $G_{(m=M+1)}$. After execution of the abovementioned processing, the first measurement is completed. In this embodiment, it is so arranged that further measurement is repeatedly continued for N' times (normally, N' is three to ten times). After this repeated measurement is completed, the following arithmetic is carried out at step #31:

$$\frac{1}{N'} \sum_{i=1}^{N'} \log \frac{I_{IRi}}{I_{Ri}} \qquad (2)$$

wherein, $I_{IRi}$: measured value on the infrared light which is transmitted through the measure object (at measurement of No.i)(Gain×A/D conversion value);

$I_{Ri}$: measured value on the red color light which is transmitted through the measured object (at measurement of No. i)(Gain×A/D conversion valve).

And, arithmetic of the value showing dispersion on the measured values is carried out at step #32, similarly to being carried out under the processing of the zero-point adjustment at step #9. The purpose of this arithmetic is similar to the previous. That is, the warning indiction at step #33 is made in case there is dispersion on the measured values, caused by influence of the outside light such as the alternating light or mispositioning of the measured object. Then, further action follows, i.e., measuring again. In case there is not dispersion on the measured values, the program advances to step #34, and at step #34, arithmetic of difference between the calculated values according to the equation (2) and the calculated values according to the equation (1) is carried out. Namely, $$\frac{1}{N'} \sum_{i=1}^{N'} \log \frac{I_{IRi}}{I_{Ri}} - \frac{1}{N} \sum_{i=1}^{N} \log \frac{I_{0IRi}}{I_{0Ri}}$$

The above-mentioned equation can be changed as follows since the first term shows the logarithm of the ratio of the light quantities at the time when the measured object is inserted into the measuring path, and the second term shows the logarithm of the ratio of the light quantities at zero-point adjusting.

$$\log \frac{I_{IR}}{I_R} - \log \frac{I_{0IR}}{I_{0R}} \qquad (3)$$

Assuming that the light which is transmitted through the green leaf of the measured object is represented by Lambert-Beer's formula, the following equations can be set up:

$$I_{IR} = I_{0IR} \cdot F_{IR} \cdot e^{-\delta_{IR} \cdot C_c \cdot dc}$$

$$I_R = I_{0R} \cdot F_R \cdot e^{-\delta_R \cdot C_c \cdot dc} \qquad (4)$$

Wherein, $F_{IR}$, $F_R$: damping quantity of the infrared light and the red color light caused by absorption, scattering and reflection of green leaf tissue, correspondingly;

$\delta_{IR}$, $\delta_R$: absorption coefficient of the chlorophyl against the infrared light and the red color light, correspondingly;

dc: equivalent optical path length of the chlorophyl.

Now, when putting the equation (4) into the equation (3), the following equation can be obtained:

$$\log \frac{I_{IR}}{I_R} - \log \frac{I_{OIR}}{I_{OR}} = \log \frac{F_{IR}}{F_R} + (\delta_R - \delta_{IR}) \cdot C_c \cdot dc. \quad (5)$$

Namely, the above equation (5) shows a linear equation represented by a product of the chlorophyl density and the optical path length. Therefore, the value reflecting the chlorophyl density of the green leaf can be obtained by the above-mentioned equation (5). Accordingly, the chlorophyl density calculated thus is indicated at step #35.

Figure 8:
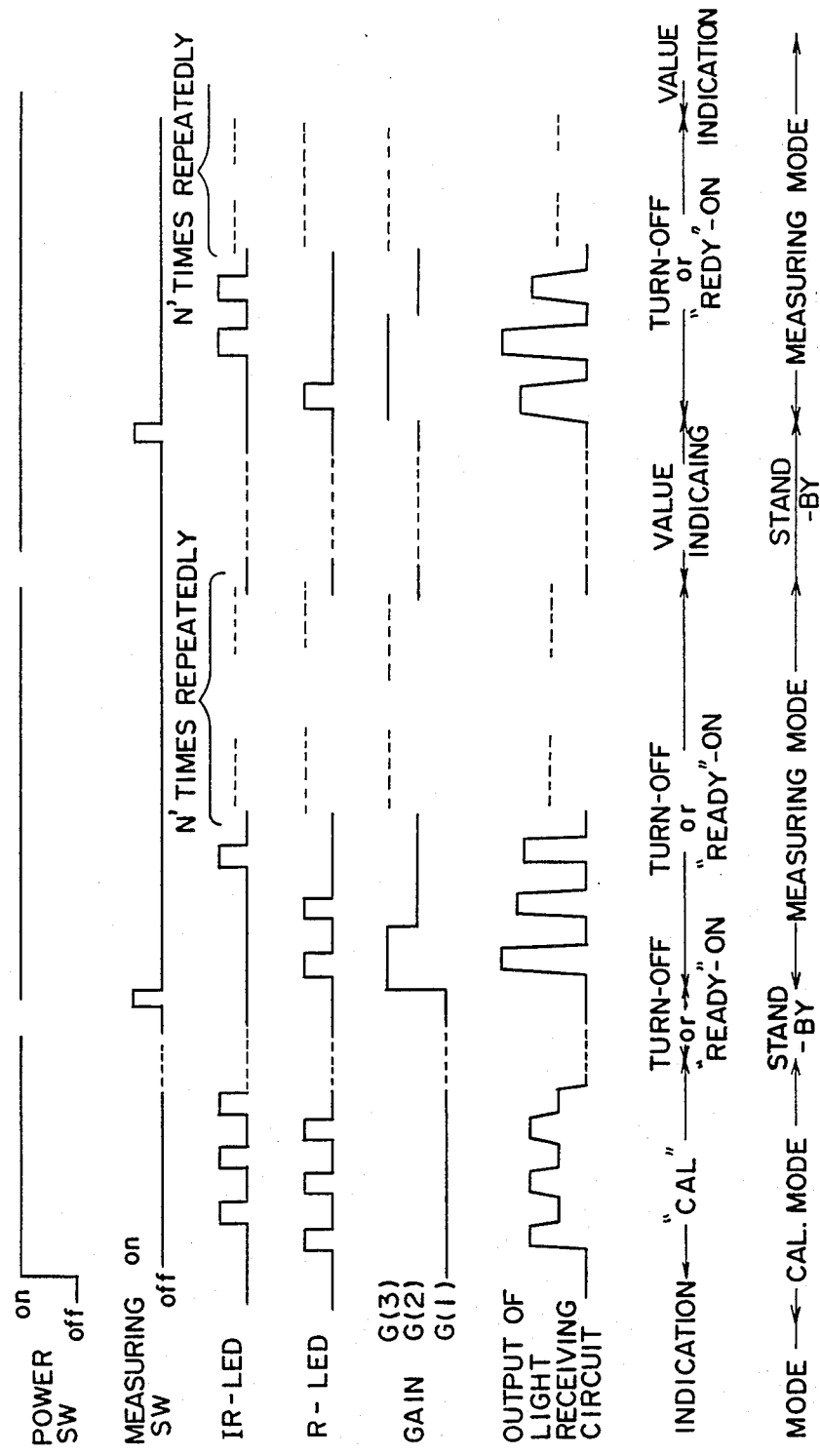
FIG. 8 is a time chart showing an operating state of respective elements of the detector.

Referring now to FIG. 8, there is shown contents, as drawn by a style of a timing chart, which are mentioned in flow charts of FIG. 6 and FIG. 7, respectively. In FIG. 8, as soon as a switch for power is turned on, the red color light and the infrared light are emitted in order under a state of the minimum gain of the current-voltage conversion circuit 5, and intensity of the transmitted light through the measured object can be obtained as outputs of the light receiving element 4. The value equivalent to the calculated values by the equation (1) can be obtained by putting these outputs into the equation (1). At the next step, the green leaf is inserted. Under a state of the leaf being inserted, the measuring switch 15 is made. Then the red color light is emitted, and a check is made regarding the overflow of the A/D conversion. Under the state of the maximum gain of the current-voltage conversion circuit 5, it is detected that the overflow happens, so that gain is shifted to a gain having a value at one step less, and the red color light is emitted again, and the A/D conversion is carried out. Wherein, if the overflow does not happen, then the A/D conversion value is memorized. At a further step, the infrared light is emitted, and the A/D conversion is carried out. If there is no overflow, the A/D conversion value is memorized. As measurement is repeatedly executed for N' times from the beginning, the value equivalent to the equation (2) is calculated. From these measured values, the value to be indicated is calculated, and it is indicated. The second actuation of the measuring switch shown in FIG. 8 (on the right side) means a following case. That is, it is a case that the chlorophyl density becomes higher than the previous and the A/D conversion at the red color light emission can be made under the maximum gain, while the A/D conversion at the infrared light emission can be made under the state of gain being one step less.

Figure 9:
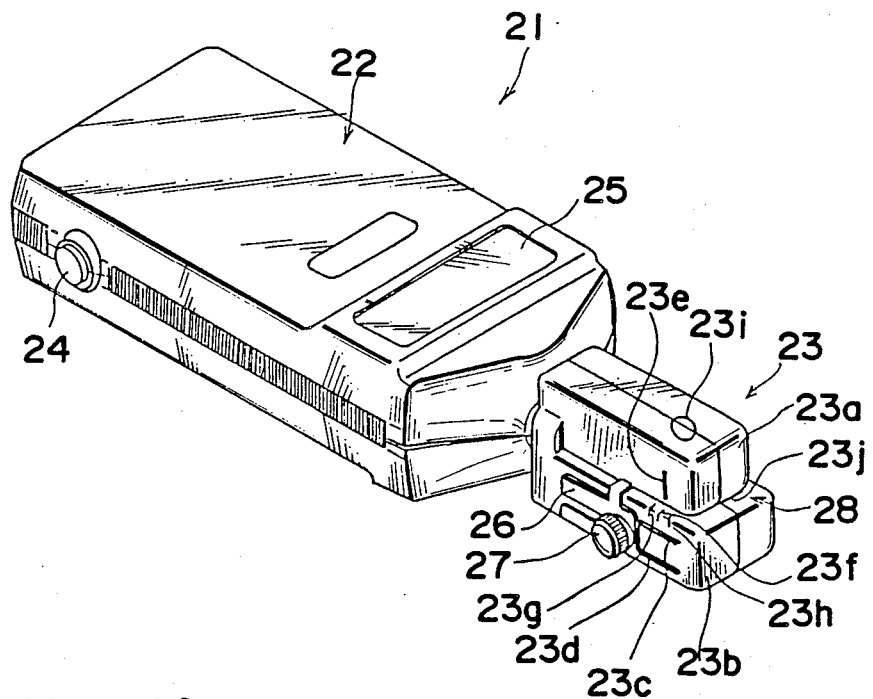
FIG. 9 is a perspective illustration showing an outside view of the detector according to one preferred embodiment of the present inventions.

Referring now to FIG. 9, there is shown a chlorophyl detector, of which the outside view is drawn there, according to this embodiment. The chlorophyl detector 21 comprises a body 22 which is pocket-sized for putting on a palm and a measuring head section 23 for measurement. In the body 2, the several circuits and units described previously are accommodated. The reference numeral 24 designates a push button associated with the afore-mentioned measuring switch 15 for switching on, and the reference numeral 25 designates a displaying window for indicating measurement information. The measuring head section 23 is fixed at the body 22 and has a fork-like-shape in order to insert the measured object. For explaining a structure of the measuring head section 23 in detail, the measuring head section 23 comprises a first head 23a and a second head 23b. Between the first and second heads 23a, 23b, a certain clearance like a slit with opening only at a front end is provided, so that the measured object may be inserted into the clearance from the front end of the measuring head section 23. Namely, the clearance makes a slit measuring part 28 for inserting the measured object. Furthermore, in the first head 23a and the second head 23b, the light emitting diode LED and the light receiving element 4 as show in FIG. 5 are respectively accommodated.

In addition to the above, in the measuring head section 23, a stopper 26 is provided, by which an inserted amount of the measured object can be controlled. The stopper 26 has a straddle-type-shape having slotted holes for a guide on side plates and is slidably supported onto the second head 23b while being guided by pins associated with the slotted holes, which are, respectively, arranged on side walls of the second head 23b. The reference numeral 27 designates one of the above-mentioned pins 27 for guiding the stopper 26, and the pins 27 have a thread screw, so that a position of the stopper 26 may be changed by loosening these pins 27. Also, by fastening these pins 27, the stopper 26 can be fixed at a desirable position.

Both reference numerals 23c and 23d designate, respectively, guide ribs like a projection arranged directly on the side walls of the second head 23b. A purpose of providing these ribs 23c, 23d is to avoid a sliding defect which is caused by a direct contact of the side plate of the stopper 26 to the side wall of the second head 23b. Both reference numerals 23e and 23f designate, respectively, indicating marks for indicating a center position of the optical path, and both reference numerals 23g and 23h designate, respectively, indicating marks for indicating each boundary of a measuring area, i.e., a diameter of the optical path on the light receiving side. The reference numeral 23i designates a indicating mark for indicating the measuring area, similarly.

In addition, as is apparent from the drawing of FIG. 10, the whole sizes of the respective heads 23a, 23b are different, i.e., the second head 23b is formed slightly bigger that the first head 23b, since the second head 23b has a function as a sample stage, so as to be easily able to insert the green leaf of the sample (measured object). As having a similar purpose, the first head 23a has a taper-shaped part 23j at a lower portion of its front end part.

The chlorophyl detector having the structure mentioned above, according to this embodiment enables an operator to measure easily the contained chlorophyl in the green leaf by taking the following steps for measurement. That is, when measuring a sample of the green leaf;

(a) at first, inserting the sample into the slit measuring head part 28 from the front end of the measuring head section 23;

(b) positioning the sample for measurement at the optical path on the light receiving side, i.e., an operator just handles it to make a spot in the sample, where the chlorophyl density must be measured, positioned between the first and the second heads 23a, 23b while looking at the respective indicating marks 23g, 23h and 23i as reference for positioning;

(c) depressing the button 24 of the measuring switch 15;

(d) waiting a few second, then the measured value (chlorophyl density) appears at the indication window 25. The zero-point adjustment, of course, must be done before taking the actual measuring step described above. Furthermore, in the case of a continuous measurement to the green leaf having a similar shape, the stopper 26 must be serviced by of an operator. Namely, before taking the measurement of a green leaf, the stopper 26 may be fixed at a proper position for measurement. After the stopper 26 is fixed once, the only action to be requested of the operator for measurement is that the green leaf is inserted to the stopper 26 at which time the green leaf touches, because positioning of the green leaf for measurement can be made by the stopper 26 due to the similar shape of the green leaf.

The above-mentioned embodiment is provided with a function of checking whether or not the measured values are influenced from an outside light as well as the timed deterioration of the light emitting diodes by detecting dispersion on the measured values, in order to maintain and improve the reliability of measurement, whereby the remeasurement can be ordered. But, the re-measurement is time consuming. Therefore, in order to save time, a chlorophyl detector had better to have correction means for compensating the timed deterioration of the diodes, especially against change of the temperature of light emitting diodes themselves and an ambient atmosphere temperature.

Another embodiment of the present invention as disclosed below is a chlorophyl detector having a function of compensating for any change of the temperature during measurement. Differences between the first embodiment described previously and this embodiment are mainly as follows. Namely, this embodiment has a temperature measuring circuit and has a different structure around a measuring head section. Of course, a program for controlling measurement is changed, if required.

Figure 11:
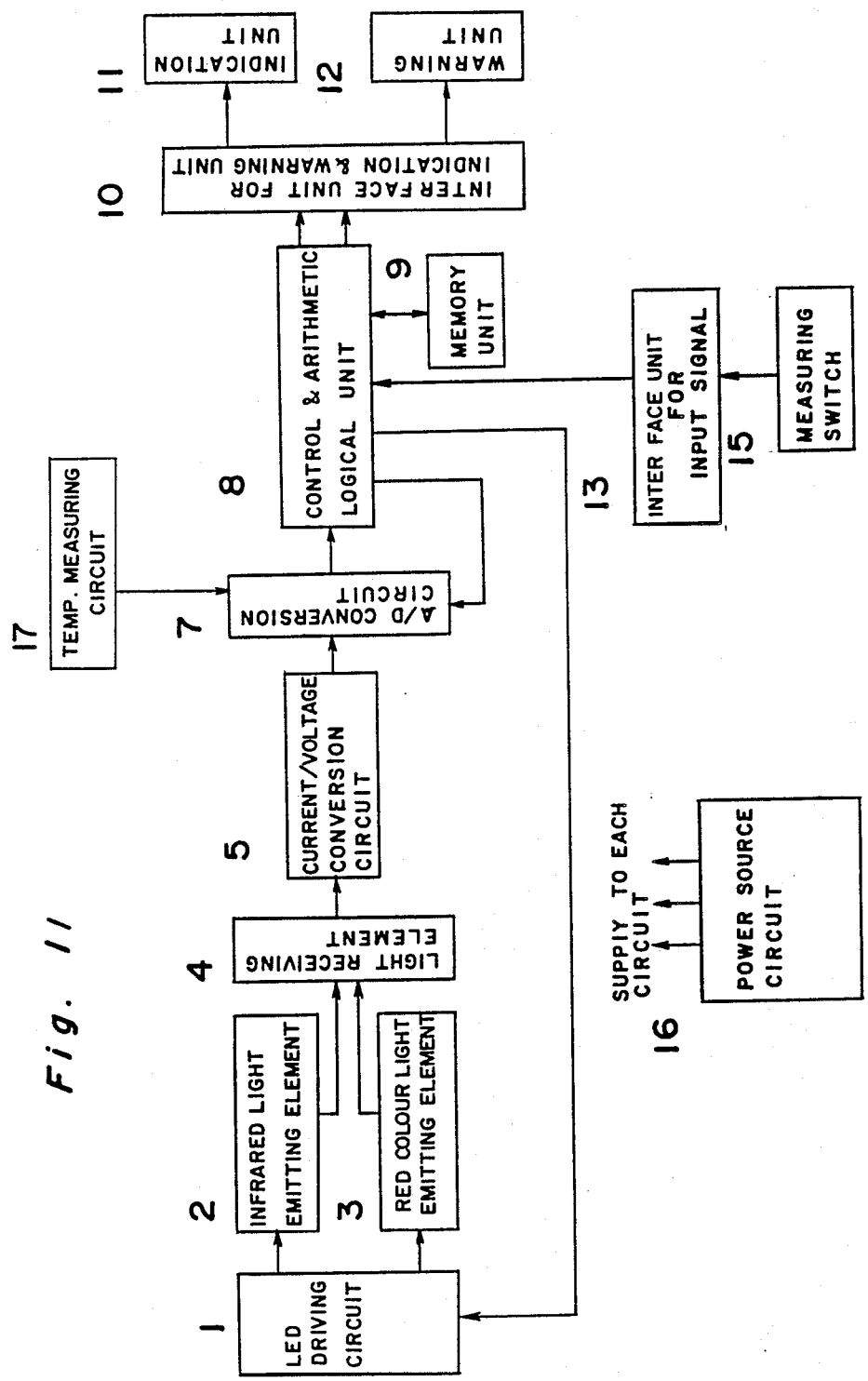
FIG. 11 is a block diagram showing components of another chlorophyl detector according to another preferred embodiment to which the present invention is applicable.

Referring now to FIG. 11, there is shown the main components of another chlorophyl detector according to the second embodiment to which the present invention is applicable. As compared with FIG. 1 in the first embodiment, difference between both figures can be easily found. One is to add a temperature measuring circuit 17 and the other is to eliminate the gain change-over circuit 6 and the pulse generator 14. In connection with an arrangement of the temperature measuring circuit 17, the gain changeover over circuit 6 can be eliminated. The functional relationship between other components and the temperature measuring circuit 17, by which the gain change-over circuit 6 is displaced, is explained and will become clear, later on, in the description. Elimination of the pulse generator 14 has nothing to do with the present invention from a technical point of view. It has something to do with an operation of the chlorophyl detector. So there is not any special meaning for eliminating it in this embodiment. The respective components shown in FIG. 11 have the same function as the corresponding components shown in FIG. 1, respectively, except for the temperature measuring circuit 17. Therefore, the temperature measuring circuit 17 is only explained below. This temperature measuring circuit 17 is means for measuring a temperature of both light emitting diodes 2,3 and of the light receiving element 4 so as to compensate for change of characteristic of both diodes 2,3 and the element 4 caused by changing of their temperatures. An output signal of the temperature measuring circuit 17 is inputted to the A/D conversion circuit 7. The memory unit 9 is means for memorizing data described in the first embodiment as well as data of the temperature characteristic about an emitted light quantity and a peak-wavelength of both the light emitting diode 2 for emitting the infrared light and the light emitting diode 3 for emitting the red color light and an output of the light receiving element 4.

Figure 12:
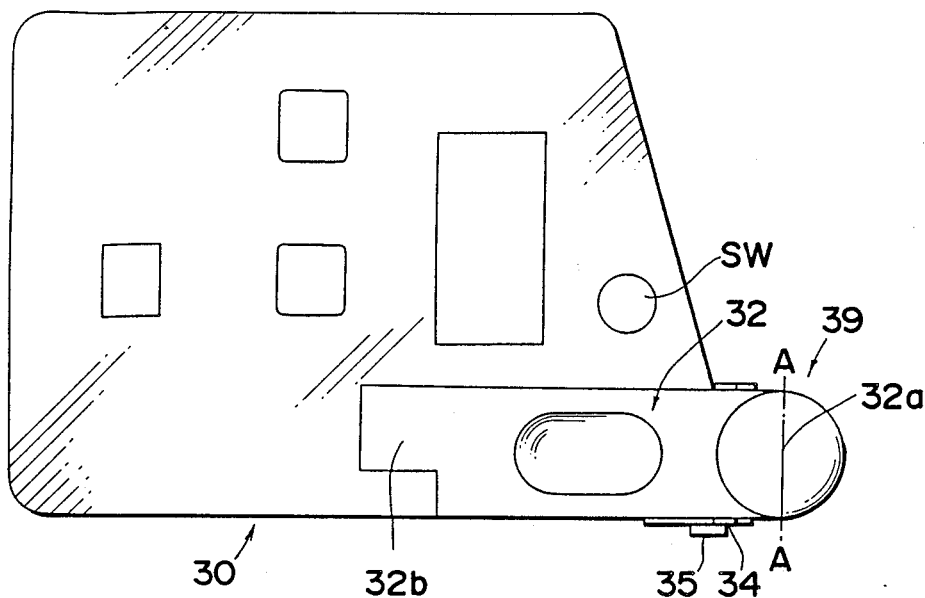
FIG. 12 is a front elevation view of the abovementioned detector shown in FIG. 11.
Figure 13:
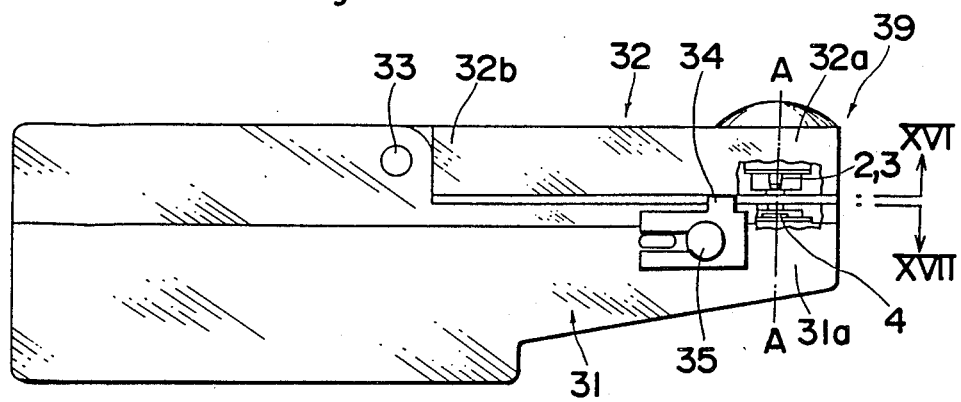
FIG. 13 is a side elevation view of the detector shown in FIG. 12.

Referring now to FIG. 12 and FIG. 13, there are, respectively shown a chlorophyl detector according to this embodiment. There is a difference in the structure between the first embodiment and the above-mentioned embodiment. That is, the measuring head section of the chlorophyl detector according to the first embodiment is a fixed-type, while the measuring head section of the chlorophyl detector according to this embodiment (the second embodiment) is an adjustable type. There is in the difference on other basic structures between both detectors.

Figure 16:
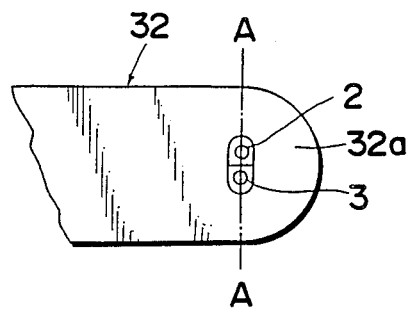
FIG. 16 is a segmentary view of the detector, viewed from the direction of an arrow mark XVI in FIG. 13.
Figure 17A:
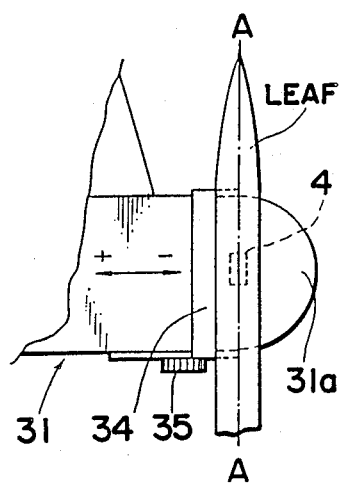
FIG. 17A and FIG. 17B are, respectively, segmentary views of the detector, viewed from the direction of an arrow mark XVII in FIG. 13, and the drawing of FIG. 17A shows a state of measuring a wide leaf and the drawing of FIG. 17B shows a state of measuring a wide leaf.
Figure 17B:
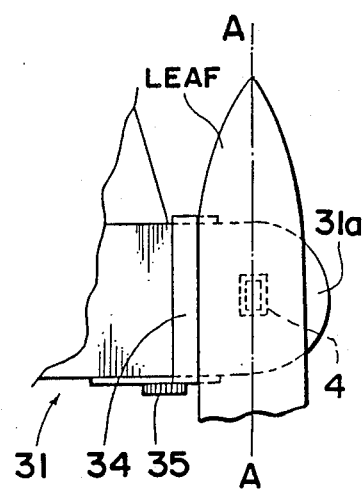

In FIG. 12 and FIG. 13, a reference numeral 39 designates a measuring head section corresponding to the measuring head section 28 in FIG. 10. The measuring head section 39 in this embodiment comprises a first head 32 and a second head 31. In the respective heads 32, 31, the light emitting diodes 2,3 for emitting, correspondingly, the infrared light and the red color light, and the light receiving element 4 are, respectively, accommodated. The above-mentioned structure is the same as the structure of the first embodiment. In this embodiment, however, the first head 32 is rotatably supported at a body 30 of the detector with a pin 33, so that the first head 32 can be rotatably moved against the second head 31. Moreover, the first head 31 is urged by a spring, which is not shown, in the opposite direction of the second head 32. So, normally, the measuring head section 39 is opened like the mouth of alligator. The respective reference numerals 34, 35, designate a stopper and a pin which are, respectively, corresponding to the stopper 26 and the pin 27 in FIG. 10. These members 34, 35 have the same structure and function as the previous. The reference numeral 32b designates an arm by which the first head is comprised, and the reference numeral 32a designates a front end portion of the first head 32, in which two diodes 2,3 are accommodated as shown in FIG. 16. The two light emitting diodes 2,3 enclosed in a small package are arranged close to each other on the line A—A. The reference numeral 31a designates a front end portion of the second head 31, in which the single light receiving element 4 is accommodated. The second head 31 is used, in common, as a sample stage. FIG. 17A and FIG. 17B show a measuring state of a green leaf. As is apparent from these drawings, by adjusting a position of the stopper 34, positioning on the sample stage, i.e., the front end portion 31a of the second head 31, can be properly done like FIG. 17A for a slim leaf and FIG. 17B for a relatively wide leaf. Especially, for slender leaves having a parallel veins of a leaf such as a leaf of the rice plant or the like, the above-mentioned arrangement for the two light emitting diodes 2,3 is suitable for measuring the chlorophyl density since the possibility that the light emitted from the respective diodes 2,3 is transmitted through the veins of a leaf can be reduced by position adjusting of the sample. Accordingly, a measuring error can be reduced, which is caused by transmitting of the light at the veins of a leaf. This is one advantage of the detector.

Figure 18:
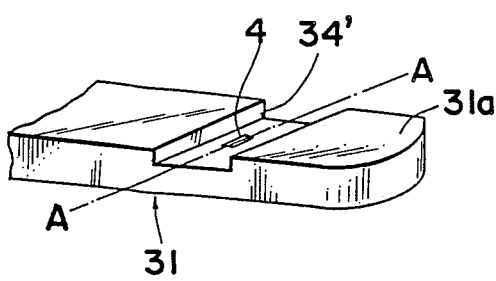
FIG. 18 is a perspective view showing one modification of a part around a measuring head section of the detector, which is corresponding to the drawing of FIG. 17A or FIG. 17B.

Then, it does not matter that the two light emitting diodes are not exactly arranged on the line, i.e., it does not matter that the veins of a leaf make a slight angle with the line passing through each center of the light sources. Instead of the stopper 34 described previously, a groove 34' parallel to the line A—A shown in FIG. 18 serves to position of the sample which is, mainly, of the slender leaf.

Figure 14:
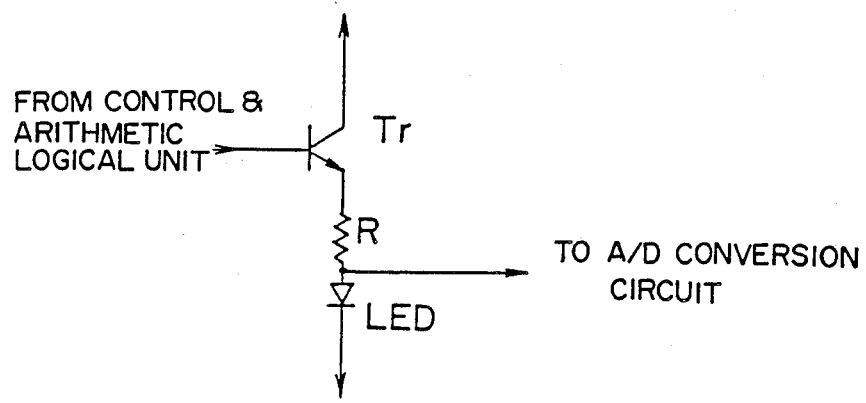
FIG. 14 is a circuit diagram, as one example, of the temperature measuring circuit shown in FIG. 11.

Referring now to FIG. 14, there is shown one example of the temperature measuring circuit 17. In the drawing, a switching transistor Tr is means for controlling an ON/OFF actuation of the light emitting diode LED while the switching transistor Tr is driven by a control signal outputted from the control and arithmetic logical unit 8. A voltage drop of a forward voltage of the diode LED can be measured by inputting an electrical potential at an anode of the diode LED into the A/D conversion circuit 7. Generally, the relation between the above-mentioned voltage drop and a temperature of the diode LED is equivalent to the relation shown with each straight line as FIG. 15. In proportion to a rise of the temperature, the voltage is reduced. A grade (a) of each line is generally constant, however, values (b) on the axis of ordinate at a standard temperature for each line are different. Therefore, in this embodiment, the values (b) on the axis of ordinate at the standard temperature on both the light emitting diode 2 for emitting the infrared light and the light emitting diode 3 for emitting the red color light are memorized in the memory unit 9, while the control and arithmetic logical unit 8 calculates the temperature (T) of the respective diodes 2,3, depending on both the above-mentioned value (b) memorized in the memory unit 9 and the inputted electrical potential (V) at the anode of the respective diodes by using the following equation;

$$T = a \cdot V + b.$$

Figure 19:
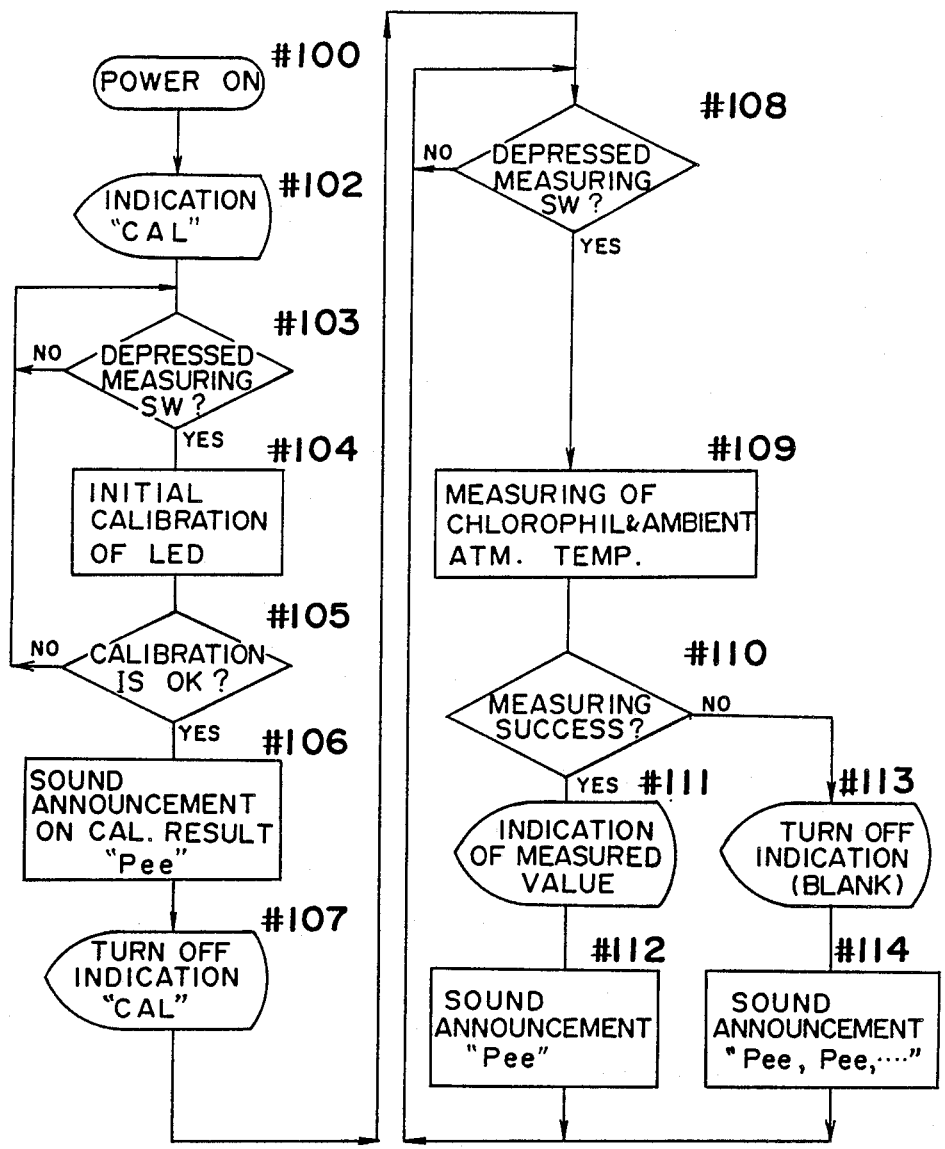
FIG. 19 is a flow chart showing an operation procedure of the detector according to the above-mentioned second embodiment.

Referring now to FIG. 19, there is shown a procedure for measuring the contained chlorophyl in a green leaf. Basically, the procedure in this embodiment is similar to the procedure in the first embodiment. However, in this embodiment, means for measuring the temperature of the light source and an ambient temperature in order to compensate measuring data is provided. Therefore, an explanation about the measuring procedure in accordance with FIG. 19 is made, mainly on compensation. The processing from step #100 to step #108 in FIG. 19 is corresponding to the processing from step #1 to step #13 in FIG. 6, and the processing from step #110 to step #114 in FIG. 19 is corresponding to the processing from step #17 to step #35 in FIG. 7. In the first embodiment, a plurality of measurement (Ntimes) for the calibration (from step #3 to step #7 in FIG. 6) and a plurality of measurement (N' times) for actual measurement (from step #18 to step #30 in FIG. 7) can be carried out, however, in this embodiment, a plurality of such measurements are not required because of providing the temperature measuring circuit 17. In addition, all processes are controlled by the control and arithmetic logical unit 8.

At first, a power switch is turned on at step #100, then the operation mode of the detector is set to a calibration mode, and "CAL" indication is made at step #102. This calibration mode means a mode for measuring the quantity of the light emitted by both diodes 2,3 and a temperature of both diodes 2,3 and of the light receiving element 4, under a state without a sample in the measuring head section 39. As described previously, the chlorophyl detector in this embodiment has an open-type measuring head section like the mouth of an alligator, and also the detector is so designed that a measuring switch is automatically turned on when the measuring head section 39 is closed. Therefore, at step #103, it is decided whether or not the measuring switch is turned on. If decided that it is turned on, then the program advances to step #104. It is, respectively, measured step #104 that the quantity of the infrared light emitted by one 2 of the light emitting diodes and of the red color light emitted by the other 3 of the light emitting diodes, and the temperature of the both diodes 2,3 and of the light receiving element 4. Then, the respective measured light quantities are, respectively, compensated by each compensation coefficient which is memorized in the memory unit 9 and is corresponding to the measuring temperature values, respectively. Thus, the incident light quantities $I_{OR}$, $I_{OIR}$ can be obtained. Next, at step #105, it is decided whether or not the abovementioned incident light quantities $I_{OR}$, $I_{OIR}$ are within a proper range which is predetermined. If decided that these light quantities $I_{OR}$, $I_{OIR}$ are beyond the proper range, for example, that light emitting diodes 2,3 are out of order or are deteriorated, or mud is attached on the light receiving element 4, the program goes to step #103 with a sound announcement, by a buzzer which is actuated by the warning unit 12, for announcing that the initial calibration has ended in failure. On the other hand, if decided at step #105 that the light quantities $I_{OR}$, $I_{OIR}$ are within the proper range, the above-mentioned light quantities $I_{OR}$, $I_{OIR}$ are stored in a RAM at the control and arithmetic logical unit 8. Then, the program advances to step #106, and the sound announcement is made at step #106 for announcing that the initial calibration has ended in success, and at step #107, "CAL" indication by the indication unit 11 is turned out.

After the processing of the calibration mode is completed, the program advances to step #108 in order to carry out the processing of the measuring mode out. At step #108, it is decided whether or not the measuring switch 15 is ON. If decided at step #108 it is ON, the program advances to step #109. At step #109, the respective temperatures of the light emitting diodes 2,3 and the light receiving element 4 are measured as well as both diodes 2,3 are actuated, and each quantity of transmitted lights from both diodes 2,3 is measured and also is compensated for the temperatures, respectively. With each of the compensated measured values $I_R$, $I_{IR}$ and the afore-mentioned respective incident light quantities $I_{OR}$, $I_{OIR}$, the chlorophyl density Cc can be calculated by the equation (5) described previously. Next, the program advances to step #110, and it is decided at step #110 whether or not the above-mentioned compensated values $I_R$, $I_{IR}$ is within a proper range which is also predetermined. If decided at step #110 the above-mentioned values $I_R$, $I_{IR}$ is beyond the proper range, the program goes to step #113. The case that the values are beyond the proper range is due to directly receiving of the incident light due to misarrangement of the sample, or the afore-mentioned problems of the light emitting diodes or the light receiving element. At step #113, no indication is made by the indication unit 11, and at step #114, the sound announcement by the buzzer s made by the warning unit 12 for announcing that measurement has ended in failure then the program goes to step #108 in order to wait an order of the next measurement. On the other hand, if it is decided at step #110 that the values are within the proper range, the program advances to step #111, and indication of the chlorophyl density Cc is made, then the sound announcement by the buzzer is made for announcing that measurement has ended in success. After that, the program goes to step #108 in order to wait the order of the next measurement.

Thus, in this embodiment, temperature measuring is executed by measuring the voltage drop of the forward voltage of the light emitting diodes, as described previously, so that the circuit for measuring the temperature is simplified. In addition, the temperature of the diodes can be measured. This is one of the advantages. Furthermore, this embodiment has another advantage in that a high accuracy and efficiency of measurement can be achieved since unexpected useless measurement can be avoided due to a misadjustment at the initial stage (at the beginning of measurement), resulting with the adjustment at the initial stage being carried out correctedly as well as reliably since measuring of the quantity of light transmitted through the sample is only started under the condition that the correct adjustment at the initial stage has been carried out. Furthermore, the sound announcement by the buzzer at the respective modes can be of service to measurement so as to reduce a measuring mistake and carry out more reliable measurement. This is another advantage for the detector.

The detailed descriptions about compensation for a temperature carried out at step #104 and step #109 in FIG. 19 by the control and arithmetic logical unit 8 are made hereinafter.

Generally, the quantity of light emitted by the light emitting diodes 2,3 is reduced in proportion to a rise of the temperature. That is characteristic in light emitting diode on the temperature. And also, the output of the light receiving elements 4 has a similar characteristic on the temperature as well. Therefore, the quantities of the incident light $I_{OR}$, $I_{OIR}$ in the equation (5) are, respectively, formulated as follows:

$$I_{OIR} = I_{osir} \text{fir}(t - ts) \quad (6)$$

$$I_{OR} = I_{osr} \text{fr}(t - ts) \quad (7)$$

where, $I_{osr}$: a generated light quantity at the red color light region at a standard temperature;

$I_{osir}$: a generated light quantity at the infrared light region at a standard temperature;

t: a temperature at measuring time;

ts: a standard temperature;

fr: a linear function of the generated light quantity at the red color light region, being characteristic of a temperature;

fir: a linear function of the generated light quantity at the infrared light region, being characteristic of a temperature.

In addition to the above, output values of the light receiving element 4 at the red color light region and the infrared light region are, respectively, formulated as each linear function being characteristic of a temperature; $\phi r(t-ts)$, $\phi ir(t-ts)$.

Furthermore, each peak-wavelength $\lambda r$, $\lambda ir$ of the emitted light of both light emitting diodes 2,3 is formulated as follows, and these are changed, being subject to change in temperature:

$$\lambda r = \lambda sr + gr(t-ts) \quad (8)$$

$$\lambda ir = \lambda sir + gir(t-ts) \quad (9)$$

where, $\lambda sr$: a peak-wavelength at the red color light region at a standard temperature; $\lambda sir$: a peak-wavelength at the infrared light region at a standard temperature;

gr: a temperature characteristic function of the peak-wavelength at the red color light region;

gir: a temperature characteristic function of the peak-wavelength at the infrared light region.

Considering temperature compensation to the output value of the light receiving element 4 and assuming that the temperature at the time when the calibration has been executed is at "tc", each quantity: $I_{cr}$, $I_{cir}$ of the incident light from both light emitting diodes 2,3, which is, respectively, measured at step #104 (FIG. 19) in the processing of the calibration mode can be formulated from the above-mentioned equations (6), (7) as follows.

$$I_{cr} = I_{osr} \cdot fr(tc-ts) \cdot \phi r(tc-ts) \quad (10)$$

$$I_{cir} = I_{osir} \text{fir}(tc-ts) \cdot \phi ir(tc-ts) \quad (11)$$

Each quantity; $I_{omr}$, $I_{omir}$ of the incident light from both light emitting diodes 2,3, which is, respectively, measured at step #109 (FIG. 19) in the processing of the measuring mode can be formulated from the above-mentioned equations (6), (7) and (10), (11) as follows, assuming that the temperature at the time when measuring has been executed is at "tm".

$$I_{omr} = I_{osr} \cdot fr(tm - ts) \quad (12)$$
$$= I_{cr} \frac{fr(tm - ts)}{fr(tc - ts) \cdot \phi r(tc - ts)}$$

$$I_{omir} = I_{osir} \cdot fir(tm - ts) \quad (13)$$
$$= I_{cir} \frac{fir(tm - ts)}{fir(tc - ts) \cdot \phi ir(tc - ts)}$$

In the equations (12), (13), each value; for, fir, $\phi r$, $\phi ir$ and the value of the standard temperature; ts are known as well as have already been memorized in the memory unit 9. Furthermore, the values; $I_{cr}$, $I_{cir}$, ts are measured values which are measured at step #104, and have been memorized in the RAM at the control and arithmetic logical unit 8, so that each quantity of the incident light from both the light emitting diodes 2,3 at the measuring mode can be calculated from the above-mentioned equations (12), (13). In addition to the above, the transmitted light quantity at the measuring mode can be calculated by compensating the output value of the light receiving element 4 by a temperature compensation. Namely, the following equations are established:

$$I_{mr} = I_{sr} \cdot \phi r(tm-ts),$$

$$I_{mir} = I_{sir} \cdot \phi ir(tm-ts)$$

where, $I_{sr}$, $I_{mr}$: a transmitted light quantity at the red color light region at a standard temperature and a measured temperature, respectively;

$I_{sr}$, $I_{mir}$: a transmitted light quantity at the infrared light region at a standard temperature and a measured temperature, respectively;

ts, tm: a standard, and a measured temperature, respectively.

Accordingly, $$I_{sr} = I_{mr}/\phi r(tm-ts) \quad (14),$$

$$I_{sir} = I_{mir}/\phi ir(tm-ts)$$
(15).

From the above-mentioned equations (14), (15), each transmitted light quantity under the measuring mode can be converted into the transmitted light quantity under a state at the standard temperature.

On the other hand, compensation of the measured value for discrepancy of the peak-wavelength of both light emitting diodes 2,3 depending on change of a temperature can be carried out as follows. As described previously, the chlorophyl density Cc in the sample is given by the equation (5), namely, $$C_c = \{\log (I_{OR}/I_R) - \log (I_{OIR}/I_{IR}) + (\log F_R + \log F_{IR})\}/(\delta_R - \delta_{IR}) \quad (16)$$

As is apparent from FIG. 10, absorption coefficient changes if the peak-wavelength is shifted. Therefore, assuming that the absorbence curve in FIG. 10 is represented by $h(\lambda)$, the denominator in the equation (16): $(\delta_R - \delta_{IR})$ can be converted as follows;

$$\begin{aligned}\delta_R - \delta_{IR} &= h(\lambda r) - h(\lambda ir) \\ &= h(\lambda sr + gr(t-ts)) - h(\lambda sir + gir(t-ts))\end{aligned} \quad (17)$$

Wherein, all data, such as the above-mentioned absorbence curve: $h(\lambda)$, each temperature characteristic function: gr, gir concerned with the peak-wavelength of both light emitting diodes 2,3, the standard peak-wavelength: λs, λsir and the standard temperature: ts are, in advance, memorized in the memory unit 9. Accordingly, compensation for discrepancy of the peak-wavelength can be calculated by the above-mentioned equations (16), (17) since a variable "t" in the equation (17) is a value of the temperature: tc, tm which is measured at the calibration mode or at the measuring mode.

Figure 20:
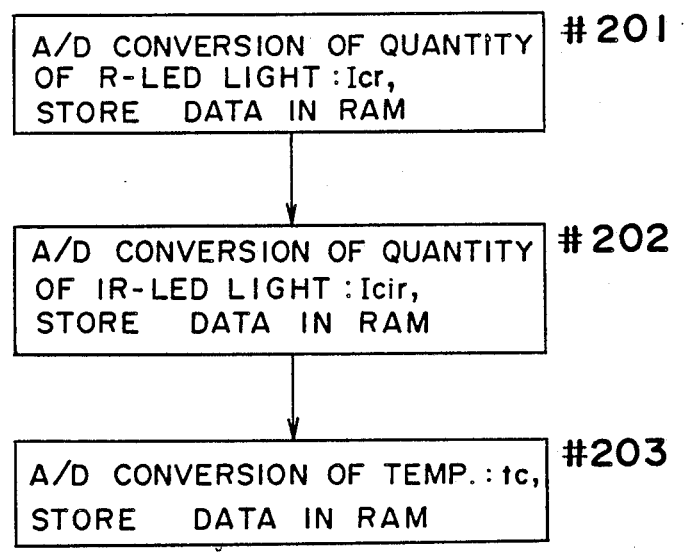
FIG. 20 is a flow chart of a subroutine which is carried out at step #104 in FIG. 19.

The procedure of the compensating process by the method of the measured value compensation described above is explained in conjunction with FIG. 20 and FIG. 21. The process which is carried out at step #104 in FIG. 19 is shown in FIG. 20. That is, at step #201, the quantity of light: $I_{cr}$ emitted from the red color light emitting diode 3 (R-LED) at the temperature: tc and the quantity of light: $I_{cir}$ emitted from the infrared light emitting diode 2 (IR-LED) at the temperature: tc are, respectively, measured at step #201 and step #202, correspondingly. And the temperature: tc at the time, when the above-mentioned measurement is made, is measured at step #203. And respective measured values are converted through the A/C conversion circuit 7 and are stored in the RAM at the control and arithmetic logical unit 8, at respective steps.

Next, the process which is carried out at step #109 in FIG. 19 is shown in FIG. 21. That is, measurement of the chlorophyl density and measurement of the temperature can be made from step #301 through step #311. The quantity of the light: $I_{mr}$ of R-LED transmitted through the green leaf and the quantity of the light: $I_{mir}$ of OR-LED transmitted through the leaf are, respectively, measured at step #301 and step #302, correspondingly. And the temperature: tm at the time, when the above-mentioned measurement is made, is measured at step #303. In addition, at the same time, the A/D conversion of the respective measured values are executed at respective steps. Next, at steps #304 and #305, compensation of the respective incident light quantities corresponding to R-LED and IR-LED is, respectively, executed by the equations (12), (13). Further, at steps #306 and #307, compensation of the respective transmitted light quantities: $I_{mr}$, $I_{mir}$ of both R-LED and IR-LED are made, similarly to the above, by the equations (14), (15). After the compensation described above, the difference of the optical density between R-LED and IR-LED is calculated by the equation (5).

As described previously regarding dispersion of the peak-wavelength of each LED 2,3, it changes within a certain range. Especially, the peak-wavelength may be shifted due to the influence of the temperature of the LED itself. In addition, since the absorbence curve of the chlorophyl is characteristic of FIG. 10, there is a possibility that the difference of the optical density between the two kinds of wavelength becomes greater if dispersion of the light emitting diode 3 for emitting the red color light becomes great even if the chlorophyl density is constant. Therefore, the compensating process for the calculated values of the optical density difference must be made by using a compensating coefficient. So, arithmetic for calculating the peak-wavelength of each LED at both the standard temperature (for example, at 0° C.) and at the temperature which is measured at step #303 is made at step #309. This arithmetic can be easily made since the shifted amount of the peak-wavelength of the LED due to the influence of the temperature is, generally, well-known to be about +0.2 nm per 1° C. After that, at step #310, arithmetic for calculating the compensating coefficient for compensation of the optical density difference which is calculated at step #308 is made depending on the peak-wavelength of each LED which is calculated at step #309. This coefficient can be calculated from the absorbence curve of the chlorophyl shown in FIG. 10, in advance and has been memorized in a ROM at the control and arithmetic logical unit 8 as a data table. Accordingly, the above-mentioned coefficient is picked up from the data table in accordance with a combination of two kinds of the peak-wavelength corresponding to the R-LED and the IR-LED, which are, respectively, calculated at step #309 by means of the table-searching method at step #310. After that, arithmetic for calculating the chlorophyl density is made at step #311, i.e., the optical density multiplied by the above coefficient.

As in this embodiment, thus, compensation for the emitting light quantity of each light emitting diode 2,3, the peak-wavelength of the emitted light and the output value of the light receiving element 4 against the change of the temperature can be made so as to make a measuring error caused by changing of the temperature less possible. It is possible to obtain efficiently a highly accurate measuring value at any time without any further calibration when the initial calibration for the light source can be done once at the beginning.

Accordingly, this embodiment has an advantage that the reliability of the detector as well as the operability of the detector can be improved remarkably.

Here are disclosed some modifications of the embodiment. Namely, regarding measuring of the light emitting diode, it is possible to measure an ambient temperature with a thermistor or the like instead of measurement of the voltage drop of the forward voltage of the light emitting diode. The sound type announcement by the buzzer can be changed to a warning lamp type announcement.

There are other ways available for the improvement of the reliability and operability of a chlorophyl detector. In the above-described embodiment, although, it is achieved by compensating measured values for factors having an influence upon the quantity of light which is emitted by the light emitting diode, such as a temperature. It is also achieved by the method that the initial calibration for the light source may be made again if a difference between the temperature at the measuring stage of the chlorophyl density and the temperature at the initial calibration for the light source is beyond a predetermined allowable range. In another embodiment described below, the above-mentioned method is applied.

Components necessary for a chlorophyl detector according to this embodiment are exactly the same as ones of the second embodiment, i.e., components shown in FIG. 11. The only difference is a program for controlling the control and arithmetic logical unit 8. Furthermore, the procedure of measurement is almost the same as the procedure of the second embodiment (see FIG. 19). The only difference is to add a process (at step #109a and step #109b in FIG. 22) deciding whether or not the change of the temperature is within the allowable range.

Figure 22:
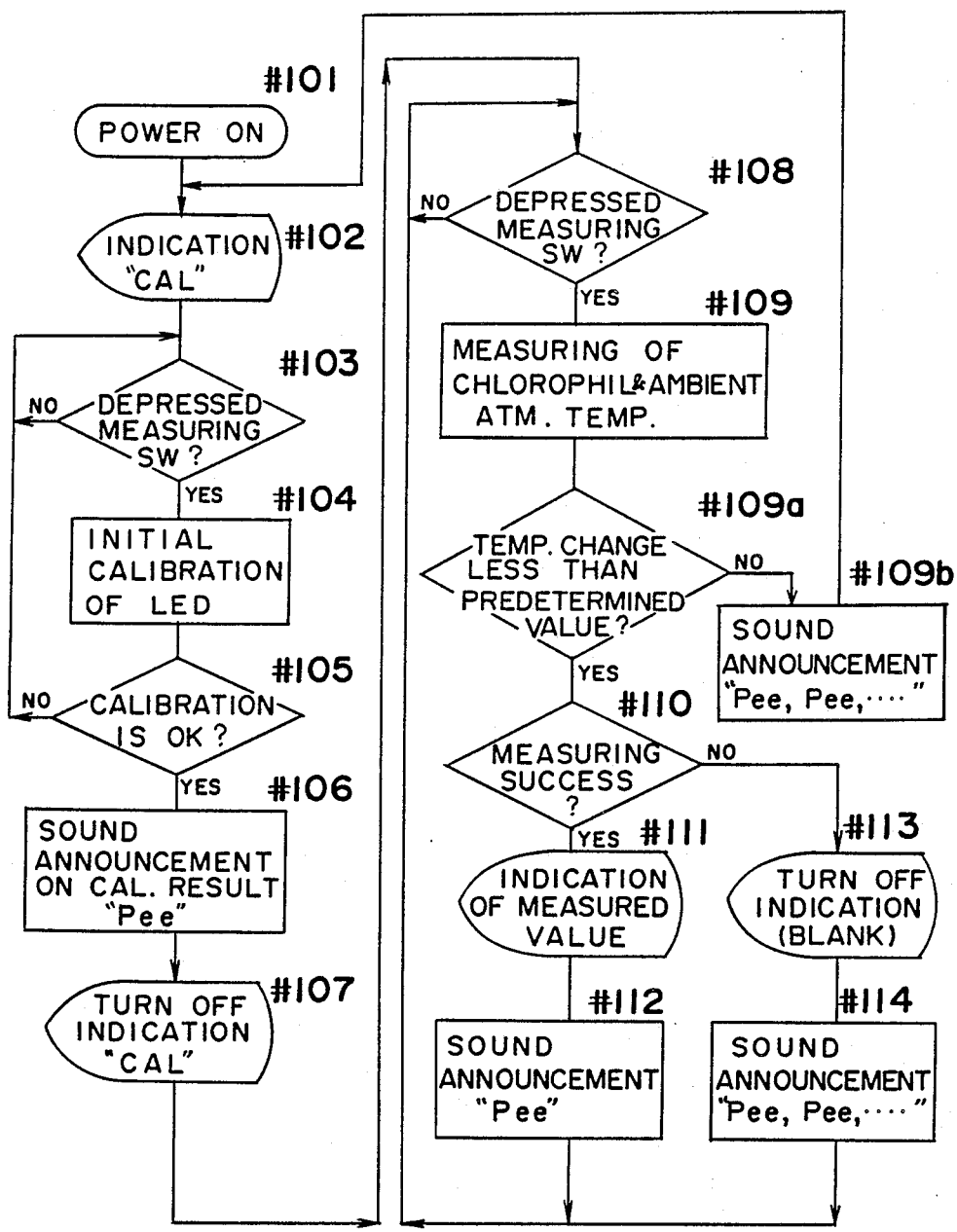
FIG. 22 is a flow chart showing a modification of an operation procedure of the detector which is partially changed as compared with the operation procedure shown in FIG. 19.

Referring now to FIG. 22, there is shown a procedure of the chlorophyl density measurement which is almost the same as FIG. 19. The contents of the process at steps from step #101 to step #108 are the same as the corresponding step (in FIG. 19) in the second embodiment. In this embodiment, data memorized in the memory unit 9 are different from data of the second embodiment. Namely, data of a predetermined allowable range dependent on the emitted light quantity characteristic of each light emitting diodes 2.3, are included in the memory unit 9. When decided at step #105 that each calibrated incident light quantity $I_{OR}$, $I_{OIR}$ which is, respectively, calibrated with a compensating coefficient memorized in the memory unit 9 is within the allowable range, the quantities $I_{OR}$, $I_{OIR}$ and the measured temperature values which are, respectively, measured at step #104 are stored in the RAM at the control and arithmetic logical unit 8. That is, in this embodiment, the above-mentioned temperature is memorized as well. There is one different process as compared with the second embodiment. After that, the same process as the processes of the second embodiment are carried out at step #106, #107, #108 and step #109, respectively. Next, at step #109a, the temperature of each light emitting diode 2,3 and the light receiving element 4, of which the values are memorized in the RAM at step #105 is compared with each present temperature which is measured at step #109, correspondingly. And it is decided whether or not the difference between two values of the corresponding temperature is within the allowable range. If decided at step #109a that it is beyond the allowable range, then at step #109b, the sound announcement by the buzzer is made, and the program goes to step #102 in order to make the initial calibration again. If decided at step #109a that it is within the allowable range, then the program advances to step #110, and after that, the same processes as the process of the second embodiment are carried out at step #110, #111, #112, #113 and #114, respectively. That is, there is another different processing at step #109a as compared with the second embodiment. That is, if the difference between the temperature values measured at the initial calibration stage and at the actual measuring stage becomes so much, the quantity of the light emitted by the light emitting diodes 2,3 and the light receiving quantity received by the element 4 at the respective stages must deviated from each other. It means that measuring values are not correct if measurement is be done without regard to such a change of the temperature. Therefore, in order to avoid the influence caused by the different temperature, the initial calibration can be made again, so that each temperature measured at both the calibration stage and the measuring stage become closer, then a reliable measured value can be obtained. Thus, the reliability and the operability of the chlorophyl detector can be improved, similarly to that in which the second embodiment was achieved.

Figure 23:
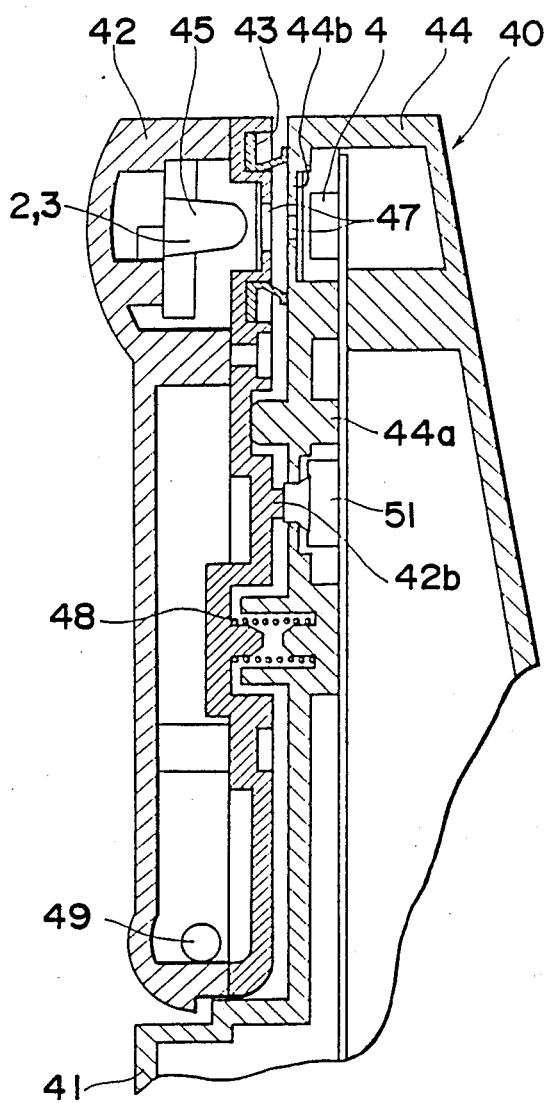
FIG. 23 is a enlarged cross sectional and partial diagrammatic view along a longitudinal direction of a measuring head section of a detector according to another embodiment to which the present invention is applicable.
Figure 24:
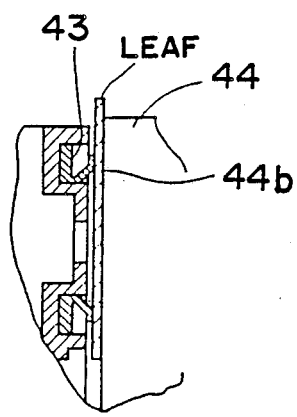
FIG. 24 is a fragmentary sectional view around a front end part of the measuring head section shown in FIG. 23.
Figure 25:
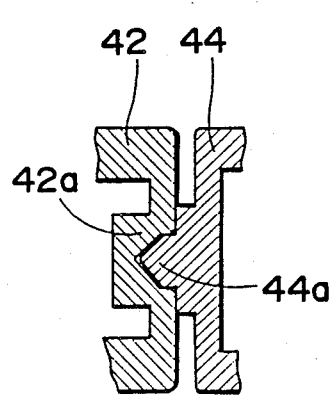
FIG. 25 is a fragmentary sectional view showing one modification of a stopper mechanism of the measuring head section shown in FIG. 23.
Figure 28:
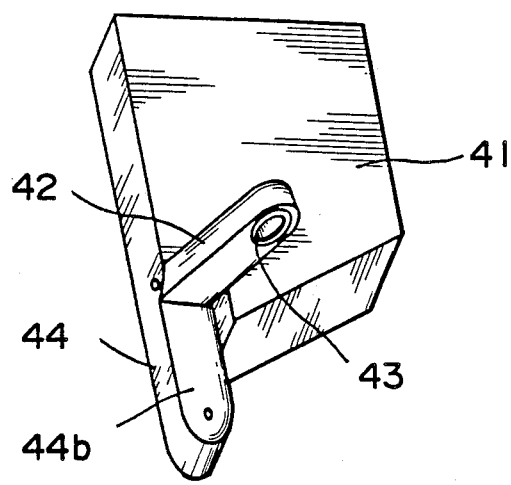
FIG. 28 is a schematic illustration of the detector shown in FIG. 23.

The description hereinbelow is with reference to the operability as well as the reliability of a chlorophyl detector, which can be improved. The description is made from a structural point of view, especially in relationship an improvement of a measuring head section of a chlorophyl detector. The chlorophyl detector in the first embodiment shown in FIG. 9 has the fixed-type measuring head section 23. That is, the first head 23a and the second head 23b are fixed at the body 22 of the chlorophyl detector 21, and there is a space between the first head 23a and the second head 23b, in which a sample of a green leaf must be inserted. In this type of detector, an inserting operation of the leaf into the space is not so easy against warped leaves. It is, of course, quite easy for plain leaves. Therefore, it is preferable that the structure of the measuring head section of the chlorophyl detector is so designed that one of the measuring heads is movable like the detector in the second embodiment shown in FIGS. 12 and 13. The drawing of FIG. 23 is equivalent to the enlarged cross sectional view along a longitudinal direction of a measuring head section in FIG. 12. In FIG. 23, the reference numeral 40 designates a measuring head section which comprises a first head 42 and a second head 44. The first head 42 is rotatably supported to a body 41 of a chlorophyl detector with a pin 49 at its one end. The second head 44 is fixed at the body as one body. The first and the second head 42, 43 are confronted by each other. The other end of the first head 42 is designed as a light emitting part 45. In the light emitting part 45, one light emitting diode 2 for emitting the infrared light and one light emitting diode 3 for emitting the red color light, which are packed in one package, are arranged. A light receiving part is arranged at the end portion of the second head 44, while facing the light emitting part 45. In the light receiving part, a light receiving element 4 is arranged so as to face both light emitting diodes 2,3. An optical measuring path is arranged between the light emitting diodes 2,3 and the light receiving element 4. The reference numeral 47 designates a window through which the lights are transmitted. The movable first head 42 is urged by the spring 48 in a direction to the opposite side of the second head 44. So normally, the measuring head section 39 looks like FIG. 28 . The reference numeral 44b designates a sample stage on which the sample of a green leaf is put. The reference numeral 43 designates a shielding member which is arranged around the light emitting part 45 so as to avoid any light coming into the optical measuring path from the outside. The shielding member 43 is made of rubber or the like and is fitted to a bottom wall of the first head 42, which is facing the sample stage 44b. Due to elasticity of the shielding member 43, the sample on the sample stage 43 is fixed steadily on the sample stage 43 like FIG. 24 without any injury, as well as the outside light having influence upon measurement can be shut out when the measuring head section 40 is closed. The reference numeral 44a designates a stopper by which a clearance between the first head 42 and the second head 44 is maintained at a certain distance as well as positioning of the sample of the leaf is fixed on the sample stage 44b. If it is difficult to position the first head 42 due to swaying of the first head 42, the structure shown in FIG. 25 serves in the positioning of the first head 42. That is, a stopper 44a' has a tapered projection at its top end, while there is arranged a tapered recession 42a on the bottom wall of the first head 42 so as to be associated with each other. According to this structure, swaying of the first head 42 can be prevented steadily and effectively. The reference numeral 51 designates a measuring switch for outputting a signal for the start of measuring when the measuring head section 40 is closed. The reference numeral 42b designates a projection arranged on the bottom wall of the first head 42, so as to actuate the above switch 51 when the measuring head section 39 is closed.

Figure 26:
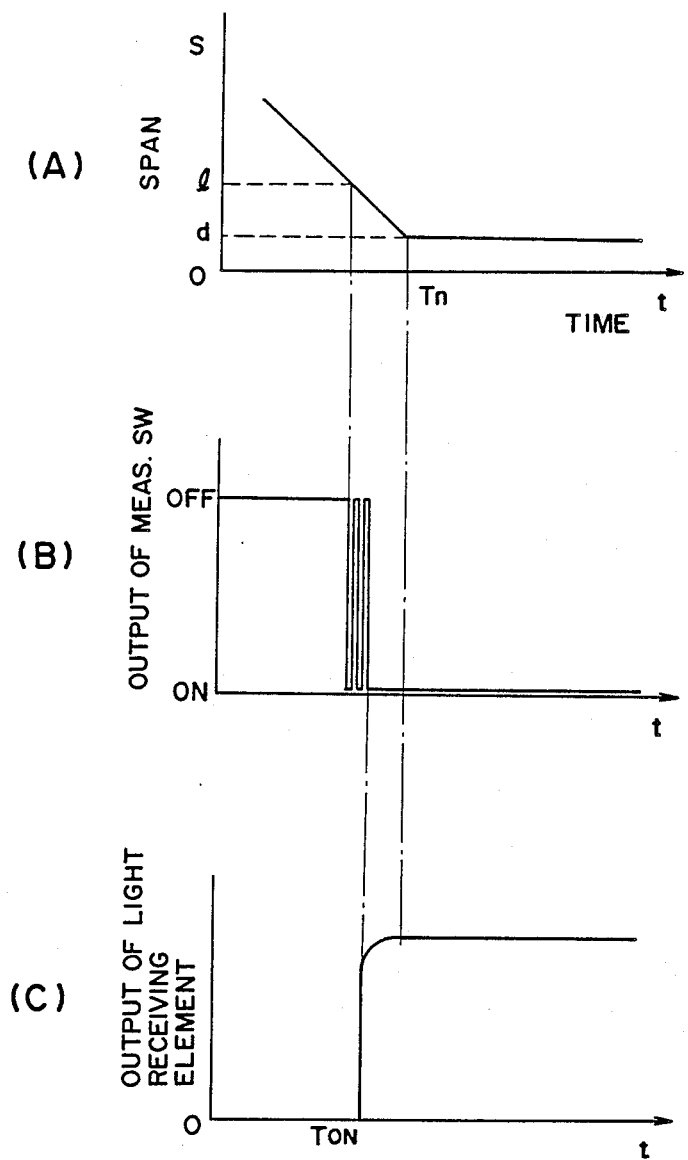
FIG. 26 is an explanatory diagram for explaining an operation at the time when the measuring head section is ready for measuring a sample, and each view (A), (B) and (C) shows, respectively, a span of a space where the sample is inserted, a state of an outputted signal from a measuring switch and a signal level outputted by a light receiving element.

Hereinbelow, a measuring procedure in this embodiment and an operation processing of the control and arithmetic logical unit 8 are explained. Basically, the procedure and the process are is similar to these in the aforementioned two embodiments. Namely, views (A), (B) and (C) in FIG. 26 show respective states of some components of the chlorophyl detector. In FIG. 26 (A) an axis of ordinate designates a span: s between the light emitting diodes 2,3 (LED) and the light receiving elements 4. When the first head 42 is moved toward the second head 44, i.e., the sample stage 44b, the measuring switch 51 is moved to a state of ON at the span: $S=l$. As the switch 51 just reaches the ON-state, a phenomenon of chattering may happen a little at that time. After finishing the chattering phenomenon, at the span: $s=d$ the switch 51 is completely turned on (see FIG. 26 (B)). After completion of the complete ON-state of the switch 51, the control and arithmetic logical unit 8 makes the LED driving circuit 1 actuated, and both light emitting diodes 2,3 start emitting the infrared light and the red color light, respectively. If the light emitting diode 2 for emitting the infrared light is actuated at a time: Ton, the light receiving element 4 starts outputting its output signal at the time: Ton with and unstable state of outputting until a time: Tn as shown in FIG. 26 (c) since the first head 42 is still on the way to its predetermined position, even if the influence of the chattering phenomenon is considered. That means the output of the light receiving element is still unstable When a time passes at a time: Tn, the first head 42 is located at its predetermined position where the first head 42 is positioned by the stopper 44a, then the output of the element 4 is moved to the stable state. Therefore, it is better to start measuring after the time: Tn. On the other hand, the A/D conversion through the A/D conversion circuit 7 is ordered to start at the time: Ton by the control and arithmetic logical unit 8, and the control and arithmetic logical unit 8 fetches a converted value for arithmetic at the time when an output level of the A/D conversion circuit 7 becomes stable. After completion of the calculation, the announcement may be made, similarly to the announcement in the aforementioned embodiment.

Figure 27:
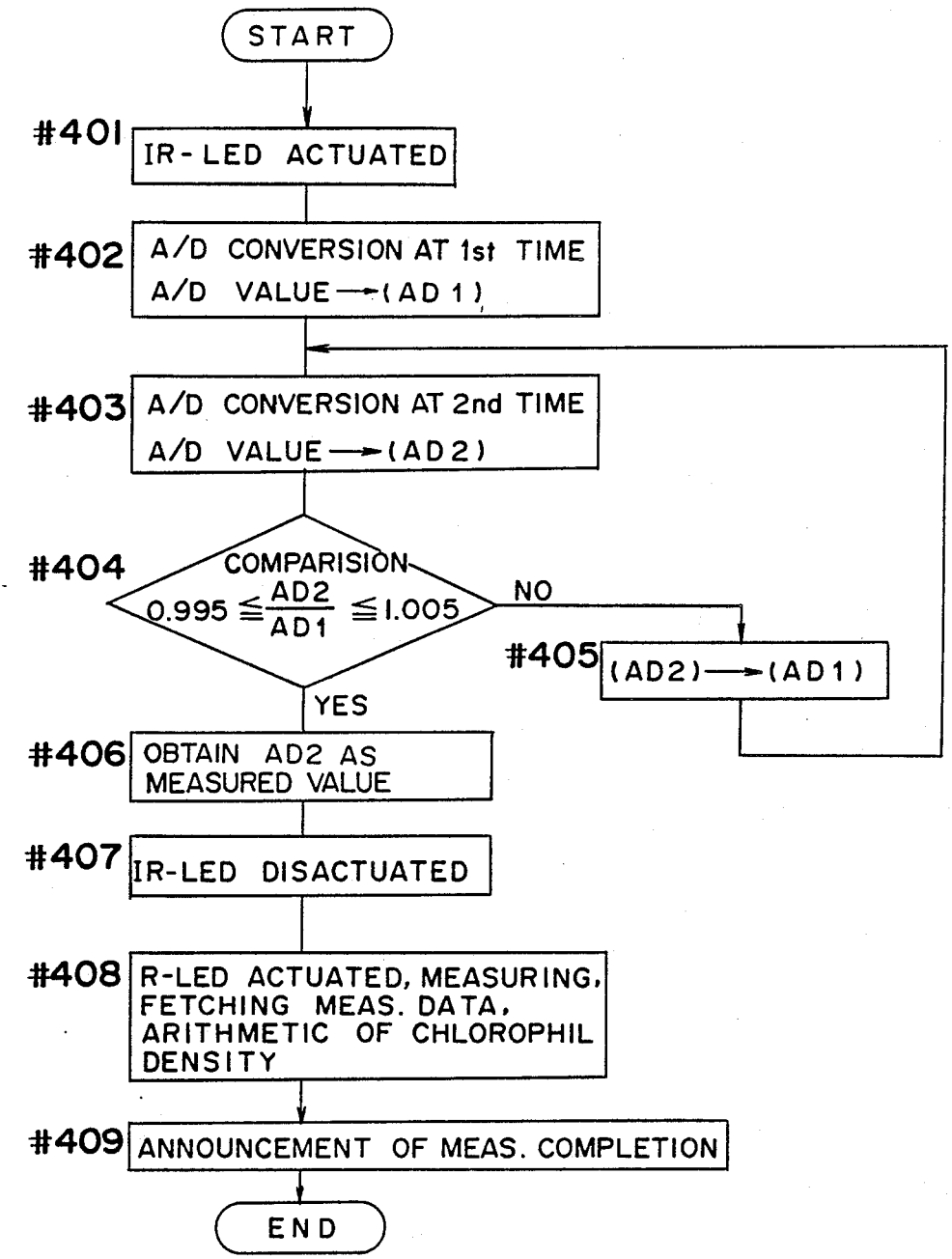
FIG. 27 is a flow chart showing another modification of an operation procedure for measuring, which is changed as compared with the procedure shown in FIG. 22 and is relating to the drawing of FIG. 26.

Referring now to FIG. 27, there is shown one example of a procedure of a measuring operation controlled by the control and arithmetic logical unit 8. In this procedure, the light emitting diode 2 for emitting the infrared light is, first, actuated, then the other diode 3 is actuated. As compared with the aforementioned embodiment, the turn of actuation is vice versa. However, there is no special meaning on discrepancy of its actuation turn in several embodiments hereinto.

At first, the light emitting diode 2 for emitting infrared light is actuated at step #401. At step #402, a first A/D conversion is made and its converted data is stored at address AD1. At step #403, a second A/D conversion is made and its converted data is stored at address AD2. Next, it is decided at step #404 whether or not the output signal level from the A/D conversion circuit 7 is stable. If accuracy of stability, for example, is set like that 0.5% of unstability is allowed, then it is decided at step #404 whether or not $0.995 \leq (AD2/AD1) \leq 1.005$ is satisfied. If decided at step #404 that ratio of the level of two output signals AD1, AD2 is within the above-mentioned range, the program goes to step #406. If it is decided at step #404 that it is not satisfied, then the program advances to step #405 so as to carry out the further A/D conversion. In this case, at step #405, the converted data stored at address AD2 is shifted to address AD1, and the further A/D conversion is carried out at step #403. This process is repeatedly executed until the above-mentioned ratio is within the arrange. At step #406, data at address AD2 is regarded as a measured value, and it is fetched into the control and arithmetic logical unit 8. This measured value was used for the calculation of a chlorophyl density, which was described previously. At step #407, the above-mentioned diode 2 is deactivated, and at step #408, the other diode 3 for the red color light is actuated and it is carried out to measure the sample and its measured value is fetched into the control and arithmetic logical unit 8. As similar to the above examples, the measured value is used for the calculation of the chlorophyl density. After the abovementioned calculation is completed, the program advances to step #409, and announcement of the measuring completion is made.

It is possible that timing for storing measurement may be changed as follows. Namely, a traveling duration from the time: Ton to the time: Tn can be predetermined by means of the results of an experiment, so that the A/D conversion may be started after passing a delay time. For example, the delay time (Tn-Ton) can be detected with the experiment. From among the detected data of the delay time: (Tn-Ton), the maximum delay time : Max. (Tn-Ton) and the minimum time: Min. Ton are picked up, then it is so designed that the A/D conversion process starts at intervals of the maximum delay time: Max (Tn-ton). If taking such an approach, it may be possible to make the measurement just by making a confirmation of the time when the measuring switch 51 becomes "ON". If a small sized microswitch having a short stroke is used as the measuring switch 51, dispersion of the time as an internal: (Tn-Ton) is so little, that it is easy to decide the maximum delay time: Max (Tn-Ton).

A combination of the above-mentioned two embodiments is available. For example, in a normal case, the A/D conversion process is repeatedly carried out until obtaining a stable signal level of the A/D conversion output, and it is designed that stable A/D conversion data are fetched into the control unit. On one hand, in an abnormal case, such as when a sample has an extremely high density or in a case that an unstable and low output signal level can only be obtained due to breaking of a wire or dirt in an optical measuring path, the A/D conversion processing is continuously repeated, too that it takes so much time or measuring may become impossible. In order to avoid such a case, it is preferable to be so designed that the A/D conversion processing is forcibly terminated in a certain time period and then measuring is forcibly finished. That is, the time limitation is of great service to measurement in this case. And if required, a system creates a warning such as "measuring range-over", or "lack of light quantity" or so on.

This embodiment has the following advantages. That is, setting of the sample is very easy. Cleaning of the light emitting part as well as the light receiving part can be made easily. There is no bad influence, such as low accuracy, owing to the movable structure of the measuring head section 40 since clearance between the first head 42 and the second head 44 is always constant Timing of starting measurement is always secured in this embodiment, so that dispersion effects on accuracy can be effectively reduced. Furthermore, when the measuring head section 40 is close, measurement is automatically executed. Therefore operability of the detector is remarkably improved. Also, the detector is applied to any shape of the leaf.

As apparent from the above-mentioned description, a measuring action of the chlorophyl density comprises an action of inserting a green leaf, an action of depressing the measuring switch button and an action of confirming indication so as to obtain the measured value in an indication window on the detector. In addition, measurement of the chlorophyl density contained in the green leaf must be repeated at several spots of the green leaf for obtaining an average value of the green leaf. Accordingly a high operability of the detector for measurement, that is, it is ensured to measure the density as well as the capability to measure it continuously is required for the chlorophyl detector. For example, in the second and third embodiment, described previously, of which the measuring head sections are of a movable type, it is recommended that the indication window for the chlorophyl density is located near the measuring head section.

Figure 29:
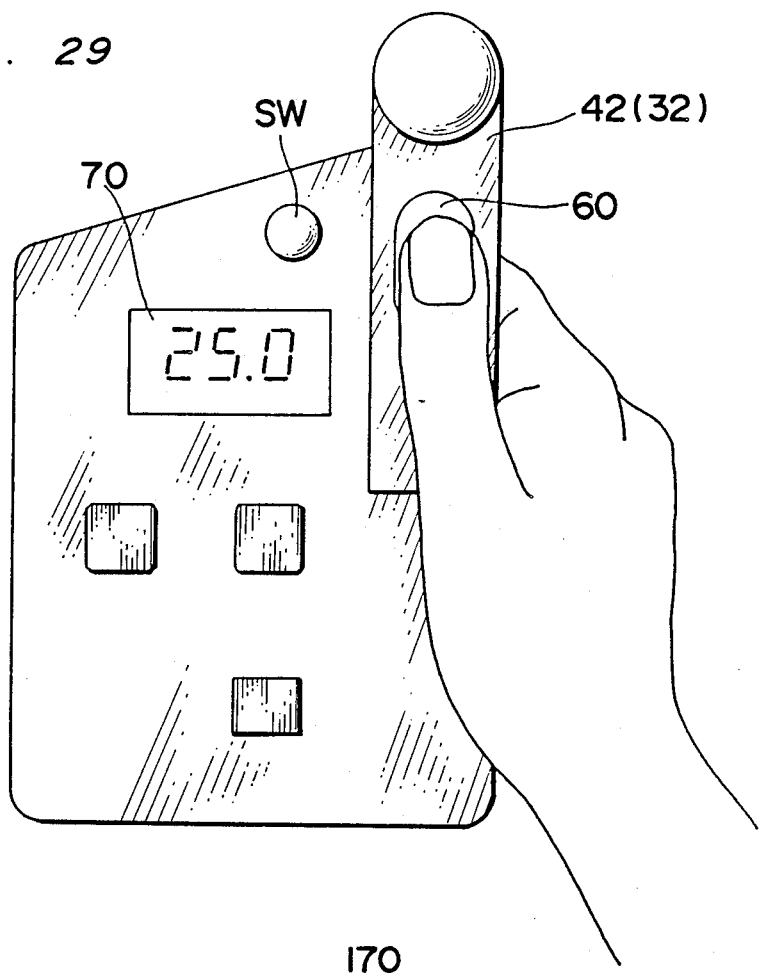
FIG. 29 is a front view showing an arrangement of the detector according to the third embodiment shown in FIG. 23.
Figure 30:
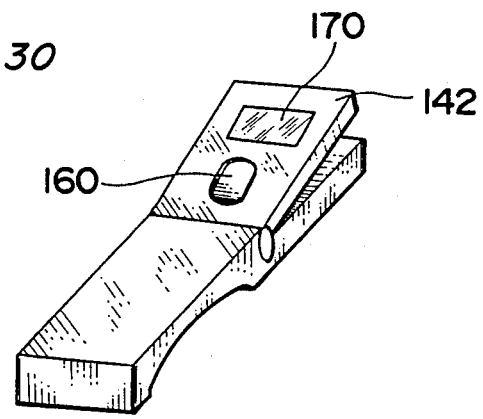
FIG. 30 is an illustration showing a modification of the detector shown in FIG. 29.

Referring now to FIG. 29 there is shown an arrangement on a front face of a chlorophyl detector, which is recommended for a detector having a movable type measuring head section, such as the detector described in the second embodiment and the third embodiment. In FIG. 29, the reference numeral 70 designates a window for indicating a measured value and other information. The reference numeral 42 (or 32) designates the first head which is rotatable, as designated in the above-mentioned embodiments. On the first head 42, a recession 60 is provided. The recession 60 is a part for depressing the first head 42 with a thumb like configuration as illustrated in the drawing of FIG. 29. The reference character SW designates a button coupled to a switch for power. As it can be seen from FIG. 29 these three components are closely located to one another on one plane, so that an one-hand-operation can be made for measurement after the power switch SW is on. Furthermore, when an operator will insert a green leaf into the measuring head section, he must watch the first head 42. At the same time, he can naturally see the indication window 70. That is, both actions for inserting and setting the green leaf to the detector and for confirming the measured value in the window 70 can be executed at the same time. Thus a continuous measuring action can be taken, so that the operability of the detector becomes high. FIG. 30 shows another arrangement of a detector. In this detector, it is possible to take a continuous measuring action. That is, a first head 142 is rotatable and has an indication window 170 and a recession 160 the same as the above. The recession 160 is arranged at a rear portion of the first head 142 and the indication window 170 is arranged at a front portion of the first head 142. In this case, a depressing action to the first head 142 can not disturb the action in which an operator confirms the measured value in the window 170.

Figure 15:
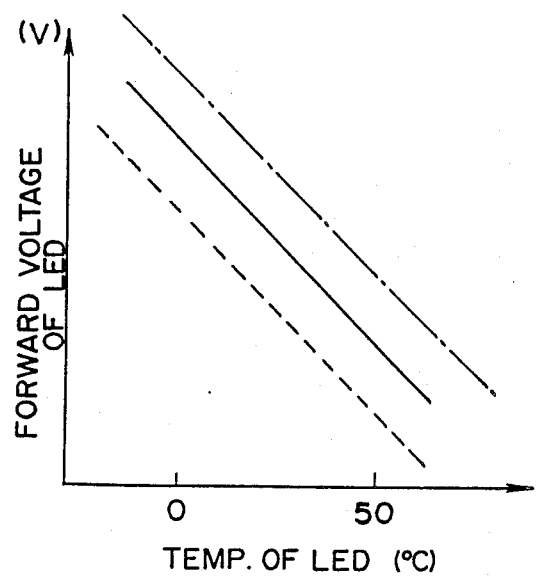
FIG. 15 is a graph showing a relation between a temperature of the LED and a forward voltage of the LED.

In the second embodiment described previously, compensation of the measured data for temperature has been explained, wherein the temperature of the light emitting diode is measured while detecting the voltage drop of the forwarding voltage of the LED, assuming that the relation between temperature of the LED and the electrical potential on the anode side of the LED is equivalent to the linear equation shown in FIG. 15 as well as each grade of the lines in FIG. 15 is equal. However, individual light emitting diodes with the same specifications might have a different output Therefore, in order to improve the reliability of the detector the grade of the LED must be considered as they may not be equal to one another. The above-mentioned second embodiment is applicable to this case without any change of the components which are provided for the detector, if the additional data and/or information are stored in the memory unit 9. Namely, these are data of each grade (a) of the linear equation represented by the equation: $T = a \cdot V + b$, of both light emitting diodes 2,3 and data of each electrical potential (b) on the anode side of the diode at a standard temperature of both diodes 2,3. If these data of each diode 2,3 are stored in the memory unit 9, temperature: T of the diodes 2,3 at any period can be calculated from the above-mentioned equation since it is designed to detect the electrical potential : V on the anode side of respective diodes 2,3 by the temperature measuring circuit 17. Furthermore, each peak-wavelength of the infrared light region and of the red color light region at the standard temperature: $\lambda sir$, $\lambda sr$, and each temperature characteristic function of each peak-wavelength at both the infrared light region and the red color light region: gir, gr are individually different. Therefore, these data are stored, in advance, in the memory unit 9. These data can be obtained with an experiment easily.

The above-mentioned way of compensating for the change of the temperature makes dispersion of the characteristic of the individual diodes reduced as much as possible, so that the effect on accuracy among detectors is minimized.

In addition to the above, the second embodiment is so designed that the difference $\Delta OD$ of the optical density is compensated with the table of the compensation coefficients (see FIG. 21 step #310). However, there is available another way of compensation.

Figure 31:
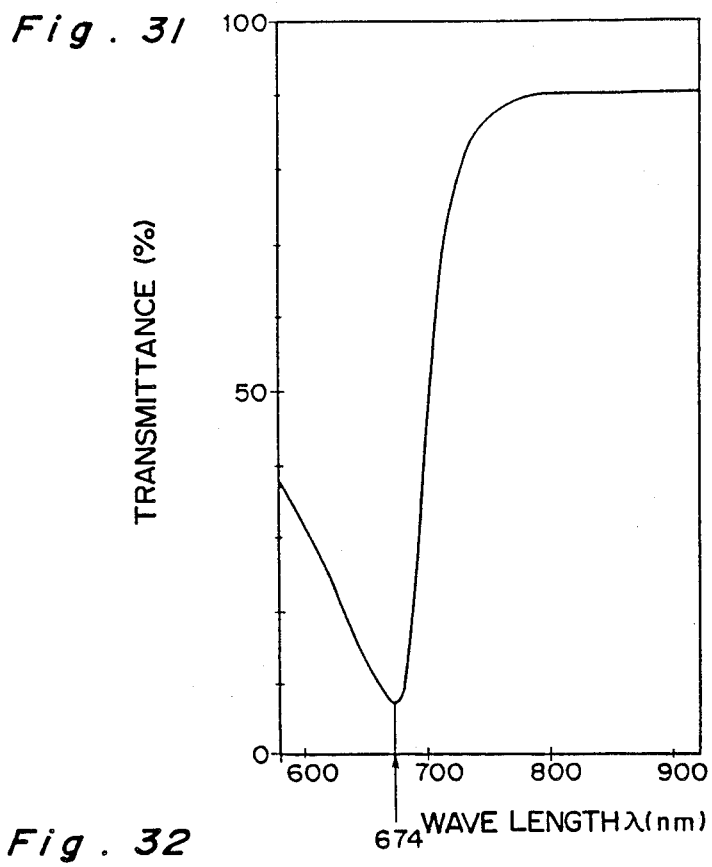
FIG. 31 is a diagram showing a curve of spectral transmission factor of a sample of a green leaf.
Figure 32:
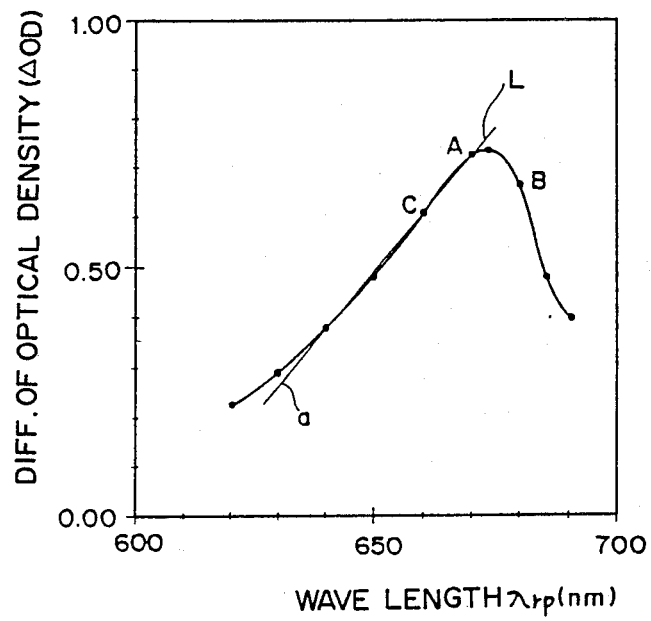
FIG. 32 is a diagram showing a curve of difference of an optical density on the chlorophyl.
Figure 33:
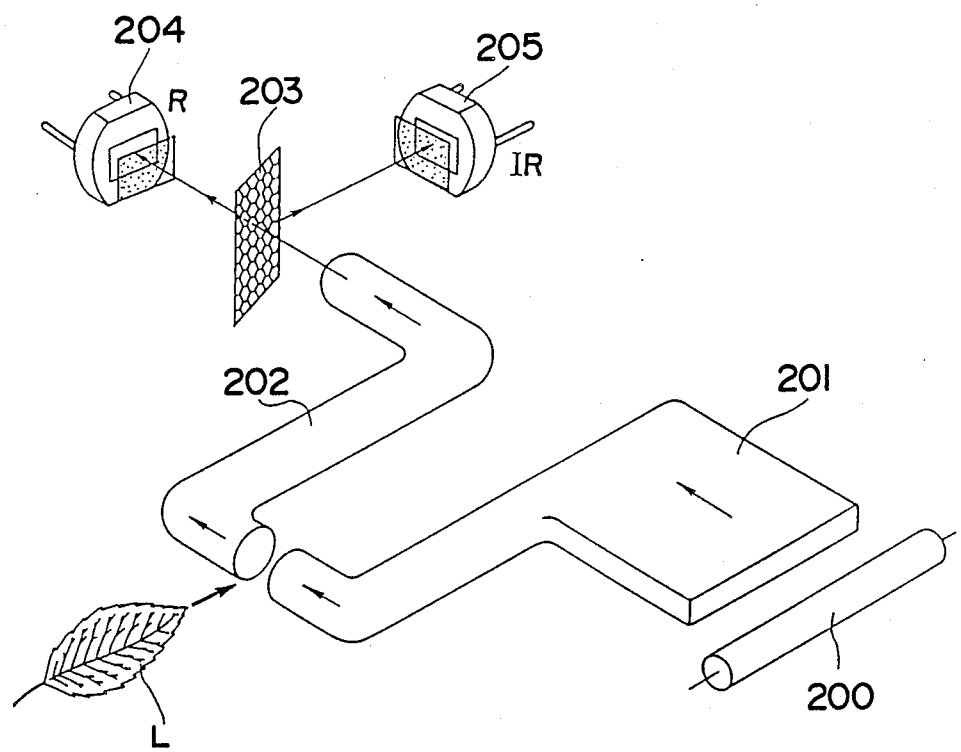
FIG. 33 is a system diagram showing one of optical density detectors in a prior art.

Referring now to FIGS. 31 and 32 there are, respectively, shown a curve of spectral transmission factor of the sample of a green leaf and a curve of "the wavelength-difference of the optical density". In FIG. 31, the curve changes remarkably in the range of the wavelength: 610–700 nm which is equivalent to the red color light region (it is called R-region, hereinbelow). Consequently, the curve of the difference of the optical density: ΔOD changes between the above-mentioned R-region and the infrared light region (it is called IR-region, hereinbelow) as shown in FIG. 32. According to a calculation, for example, the peak-wavelength is changed for 10 nm when an ambient temperature changes for 50 ° C. Therefore, the difference of the optical density: ΔOD changes approximately more than 20%. That is why compensation must be executed by the table of the compensation coefficients as described above. But, the change of the respective curves, shown in FIGS. 31 and 32, in a certain range of the wavelength is linear, so that the compensation for the temperature can be made with a calculation as a linear equation if the light having a wavelength which is in the above-mentioned range is utilized as the red color light emitted by a light emitting diode. Accordingly, the light emitting diode (R-LED) 3 for emitting the red color light of which the peak-wavelength: λrp is, at normal temperature, 640 nm≦λrp≦670 or 671 nm≦λrp≦674 is suitable for measuring the chlorophyl density. Especially, the region of the latter peak-wavelength corresponds to a part around an inflection point (674 nm), so that the change of ΔOD becomes minimized. A straight line: L in FIG. 32 is formulated as follows;

$$\Delta OD = a \cdot \lambda rp + b \qquad (18)$$
$$= 0.0113 \lambda rp - 6.852$$

Accordingly, a peak-wavelength λrp at a temperature: T° C. under measuring of the sample is given by the following equation, wherein λs : the peak-wavelength at the standard temperature: Ts °C. (for example Ts=0° C.) of the R-LED 3, ΔODs: difference of the optical density at that time, K: temperature coefficient of peak-wavelength for shifting (K=+0.2 nm/°C.);

$$\lambda rp = \lambda s + k(T-Ts) \qquad (19).$$

Therefore, the compensation coefficient for compensating the difference of the optical density: ΔOD which has been measured at a temperature: T °C. is given by the following equation;

$$\Delta ODs/\Delta OD = \Delta ODs/(0.0113 \lambda rp - 6.852) \qquad (20)$$
$$= \Delta ODs/[0.0113 \{\lambda s + K(T - Ts)\} - 6.852]$$

Here is introduced one example of a calculation regarding a measuring error. Assuming that the light emitting diodes for emitting the red color light emits a light of which the peak-wavelength is longer than the wavelength of 674 nm (an extremal value), the grade (a) of the linear equation, as apparent from FIG. 32, is −0.037. It becomes three times as compared with the value of the grade in the equation (18). This difference of the grade does not cause a problem in a normal measurement, however, in the case of misdetecting of the emitted peak-wavelength caused by some factor, the above-mentioned difference of the grade requires a result of the compensation. Namely, if the standard peak-wavelength of the R-LED 3 at a standard temperature is detected that it is 670 nm (refer to FIG. 32; at A-point), difference of the optical density: ΔOD of the sample concerning to FIG. 31 is 0.719. The measured value must be compensated so as to become equal to the above value: 0.719 no matter what the peak-wavelength is detected. For example, it is assumed that the mis-detecting happens around 679 nm in wavelength. At 679 nm in wavelength, ΔOD is 0.701. If 1 nm on the peak-wavelength is misdetected and the compensation coefficient at 680 nm in wavelength is selected, then the coefficient is 1.104 by the equation (20), so that the result after the compensation is 0.701×1.104=0.774. This value makes an error which is equivalent to 7.6% against the above-mentioned standard ΔOD (=0.719). This is a big disadvantage for the reliability of the chlorophyl detector.

On one hand, in case the R-LED 3 of which the peak-wavelength is within the range of 671 nm to 674 nm in wavelength is applied to a chlorophyl detector, the shifting amount of the peak-wavelength against the change of a temperature for ±10° C. is approximately ±2 nm in wavelength. Therefore, the peak-wavelength: λrp of the R-LED 3 is within the range of 669 nm to 676 nm in wavelength. This means that difference of the optical density: ΔOD changes very little, as it is apparent from FIG. 31, since the above-mentioned range is located closer to the inflection point of the curve. On the other hand, in case the R-LED is applied to this embodiment has a peak-wavelength less than 660 nm in wavelength (refer to FIG. 32; at C-point), the influence of 1 nm in wavelength to be misdetected is as follows. Namely, ΔOD at 660 nm in wavelength is 0.606. The compensation coefficient at 661 nm or 659 nm in wavelength according to the equation (20) is 1.209. So the result after compensation becomes 0.732. This value makes an error which is equivalent to 1.8% against the above-mentioned standard ΔOD. As described above, the R-LED 3 having its peak-wavelength from 640 nm to 670 nm at the normal temperature makes an error slight if the peak-wavelength of the R-LED 3 is misdetected at the measuring stage. Consequently, without any compensation, the measuring error becomes within ±1.7%. For example, in case a rice plant is watched for controlling its growth, there is a possibility that it is decided by the range (0.75±0.03) of difference of the optical density whether or not growth becomes good. Accordingly, the above-mentioned error range (±1.7%) does not cause any serious problem in practice. The calculation for the above-mentioned compensation is carried out at step #310 in FIG. 21 instead of the table-researching method.

If the applied R-LED has a peak-wavelength which is within the range of 671 nm to 674 nm in wavelength, the processing at step #310 and step #311 are not necessary because of the above-mentioned reason, since the abovementioned range accords to a peak of the absorbence of a green leaf. Besides, in this case, at step #309 in FIG. 21 each peak-wavelength of the light emitting diodes 2,3 is calculated, and it is decided by the control and arithmetic logical unit 8 whether or not the respective peak-wavelengths are within the range which means that it is possible to ensure the measuring accuracy if the peak-wavelength is detected within that range.

Although the present invention has been fully described by way of example with reference to the accompanying drawings, it is to be noted, here, that various changes and modifications will be apparent to those skilled in the art. Also a detector according to the present invention is applicable to detecting another specific material density contained in an object by the method utilizing difference of absorbence. Therefore, unless otherwise such changes and modifications depart from the scope of the present invention, they should be construed as included therein.

What is claimed is:

1. An optical density detector comprising:
a first light source for emitting a first light which belongs to a wavelength region in which said first light is hardly absorbed by a specific material contained in a sample;
a second light source for emitting a second light which belongs to a wavelength region in which said second light is absorbed, substantially as compared with said first light, by said specific material, wherein a peak-wavelength of said second light is shifted by change of a temperature and change of an absorption coefficient of said specific material is characteristic of a linear equation with a gentle grade;
light receiving means for measuring a quantity of said first and second lights which are, respectively, transmitted through said sample;
arithmetic means for calculating a difference of absorbence between said first light and said second light of which both change depending on the density of said specific material, on the basis of measured values measured by said light receiving means;
temperature measuring means for measuring the temperature of said first and said second light sources and said light receiving means, or measuring the ambient temperature around said first and said second light sources and said light receiving means; and
compensation means for compensating said difference of absorbence which is calculated by said arithmetic means, with an absorption coefficient of said specific material at a shifted peak-wavelength of said second light, wherein said shifted peak-wavelength is calculated on the basis of a measured value measured by said temperature measuring means.

2. An optical density detector according to claim 1, wherein said specific material is a chlorophyl, and said second light source is a light emitting diode which emits such a light having a peak-wavelength of 640 nm to 670 nm in wavelength.

3. An optical density detector according to claim 1, wherein said light sources comprise a light emitting diode for emitting a light belonging to a red color region and a light emitting diode for emitting a light belonging to an infrared region, and said specific material is chlorophyl.

4. An optical density detector comprising:
a light source;
light receiving means for measuring a quantity of light belonging to a specific wavelength region, which is selectively detected from among lights having various wavelengths which are emitted from said light source and are transmitted through a sample;
temperature measuring means for measuring the temperature of said light source and said light receiving means, or measuring the ambient temperature around said light source and said light receiving means;
memory means for memorizing information concerned with a temperature characteristic of said light source and said light receiving means about said quantity of said light, a peak-wavelength of said light and an output of said light receiving means; and
compensation means for compensating said quantity measured by said light receiving means on the basis of both said temperature measured by said temperature measuring means and said information memorized in said memory means, whereby a density of a specific material contained in said sample is detected by means of the difference of absorbence which said specific material possesses on the respective wavelengths.

5. An optical density detector according to claim 4, wherein said light source comprises a light emitting diode for emitting a light belonging to a red color region and a light emitting diode for emitting a light belonging to an infrared region, and said specific material is chlorophyl.

6. An optical density detector comprising:
a light source;
light receiving means for measuring a quantity of light belonging to a specific wavelength region, which is selectively detected from among lights having various wavelengths which are emitted from said light source and are transmitted through a sample;
temperature measuring means for measuring the temperature of said light source and said light receiving means, or measuring the ambient temperature around said light source and said light receiving means;
memory means for memorizing information which represent a relationship between a peak-wavelength of said light at respective temperatures which include, at least, two values and said respective temperatures, and information which represent a relationship between said quantity of said light emitted from said light source at the respective temperatures which include, at least, two values as well as said respective temperatures; and
compensation means for compensating said quantity measured by said light receiving means on the basis of both a measured temperature measured by said temperature measuring means and said information memorized in said memory means, whereby a density of a specific material contained in said sample is detected by means of the difference of absorbence which said specific material possesses on the respective wavelengths.

7. An optical density detector according to claim 6, wherein said light source comprises, at least, one light emitting diode, and said light emitting diode is so designated that said temperature of said light emitting diode is measured by said temperature measuring means.

8. An optical density detector according to claim 7, wherein said temperature measuring means includes means for measuring a forward voltage of said light emitting diode.

9. An optical density detector comprising:
light source means comprising a light emitting diode for emitting a red color light and a light emitting diode for emitting an infrared light;
emission control means for controlling emission of both said diodes so as to emit said red color light and said infrared light at difference times, respectively;
light receiving means having a single light receiving element for receiving each light transmitted through a sample to be measured or each light reflected on said sample, wherein said each light is emitted from said both diodes respectively; and arithmetic means for calculating a difference of absorbence on the basis of output data of said light receiving means.

10. An optical density detector according to claim 9, wherein said light source means is so designed that said light emitting diode for emitting said red color light and said light emitting diode for said infrared light emit alternatively, in response to every one signal for emission generated by a manual hand operation.

11. An optical density detector according to claim 9, further comprising a pair of heads, at least one of which is adjustable between a closed position, in which said pair of heads confront each other with a small space maintained therebetween, and an opened position in which said pair of heads are largely spaced from each other, wherein said emission control means is so designed that said light emitting diode for emitting said red color light and said light emitting diode for emitting said infrared light emit plural times at one time by turns, in response to every one signal for emission generated by a closing operation of said head.

12. An optical density detector comprising:
a first sample stage for arranging a green leaf, as a sample;
a guide member for controlling a direction to insert said leaf and being arranged on said first sample stage;
light source means comprising, at least, two light sources which emit, respectively, lights belonging to a different wavelength region and are arranged in a second sample stage facing said first sample stage, wherein said two light sources are on a straight line which makes a certain angle with said direction; and
light receiving means arranged in said first sample stage, for detecting each quantity of lights of respective said light sources, which are transmitted through said leaf, whereby density of a specific material contained in said leaf is detected.

13. An optical density detector according to claim 12, wherein said certain angle is zero degree.

14. an optical density detector comprising:
a light source;
light receiving means for measuring a quantity of a light belonging to a specific wavelength region, which is selectively detected from among lights having various wavelengths which are emitted from said light source and are transmitted through a sample;
calibration means for measuring said quantity of said light through said light receiving means at the time when said light source is actuated under a state without said sample or with a calibrating filter during a calibration stage;
discrimination means for deciding whether or not said quantity measured by said calibration means is within a predetermined range;
measurement control means for controlling to enable said light source and said light receiving means to be operated during a measuring stage when it is decided by said discrimination means that said quantity is within said predetermined range; and
memory means for memorizing said quantity measured by said light receiving means when it is decided by said discrimination means that said quantity is within said predetermined range, whereby density of a specific material contained in said sample is detected by means of difference outputting a start signal for processing measurements when said measuring head comes in contact with said positioning member.

15. An optical density detector according to claim 14, wherein said light source comprises a light emitting diode for emitting a light belonging to a red color region and a light emitting diode for emitting a light belonging to an infrared region, and said specific material is chlorophyl.

16. An optical density detector comprising:
a light source;
light receiving means for measuring a quantity of light belonging to a specific wavelength region, which is selectively detected from among lights having various wavelengths which are emitted from said light source and are transmitted through a sample;
temperature measuring means for measuring the temperature of said light source and said light receiving means, or measuring the ambient temperature around said light source and said light receiving means;
calibration means for measuring said quantity measured by said light receiving means and said temperature measured by said temperature measuring means at the time when said light source is actuated under a state without said sample or with a calibrating filter through said light receiving means and said temperature measuring means so as to obtain a calibrating value;
memory means for memorizing said light quantity and said temperature measured, respectively, by said calibration means;
discrimination means for deciding whether or not the difference between said temperature memorized in said memory means and a temperature measured by said temperature measuring means at a density measurement is within a predetermined range; and
measurement control means for controlling said density measurement and starting said calibration means again when said discrimination means decides that said difference between said two temperatures is beyond said predetermined range, whereby the density of a specific material contained in said sample is detected by means of the difference of absorbence which said specific material possesses on respective wavelengths.

17. An optical density detector according to claim 16, wherein said light source comprises, at least, one light emitting diode, and said temperature measuring means is means for measuring a forward voltage of said light emitting diode.

18. An optical density detector comprising:
a first measuring head having a light source for illuminating a sample;
a second measuring head which faces said first measuring head so that said sample is inserted between said first and said second measuring head, which have light receiving means for receiving a light illuminated from said light source and transmitted through said sample; and
an optical path which is formed between said first and said second measuring heads so that said light may be transmitted through said sample and reaches said light receiving means, one of said first measuring head and said second measuring head being rotatably supported to a body with a joint in order to move from a first predetermined position for sandwiching said sample to a second predetermined position for releasing said sample, while the other being fixed to said body, and a shielding member with elasticity being arranged on one of said first and said second measuring heads so as to surround one of said light source and said light receiving means, correspondingly.

19. An optical density detector according to claim 18, wherein said shielding member is made of a black rubber.

20. An optical density detector according to claim 18, further comprising a positioning member for positioning said measuring head at said first predetermined position.

21. An optical density detector according to claim 20, further comprising measurement control means for outputting a start signal for processing measurement when said measuring head comes in contact with said positioning member.

22. An optical density detector according to claim 21, wherein said measurement control means comprises a measuring switch which turns on when said positioning member comes into contact with said measuring head, an output circuit which is driven when said measuring switch turns on and discriminating means for deciding a stability of the level of an output signal outputted from said output circuit when receiving said output signal, whereby measurement is carried out by an output signal outputted from said discriminating means.

23. An optical density detector according to claim 18, further comprising indication means for indicating a measuring value depending on an output signal from said light receiving means, which is arranged on said body, said indication means being located close to a spot on which an operator who operates said detector can place a finger so as to move said rotatable measuring head.

24. An optical density detector according to claim 23, wherein said spot is formed at a part on said rotatable measuring head, which is located so as not to cover said indication means with an operator's hand when said operator holds said detector with one hand.

25. An optical density detector according to claim 24, wherein said spot is located on a front surface of said rotatable measuring head.

26. An optical density detector according to claim 25, wherein said indication means is arranged at a front end part of said rotatable measuring head and located closer to a front end edge of said rotatable measuring head than said spot.

* * * * *